(12) United States Patent
Ntziachristos

(10) Patent No.: US 9,226,645 B2
(45) Date of Patent: Jan. 5, 2016

(54) SYSTEM AND METHOD FOR NORMALIZED DIFFUSE EMISSION EPI-ILLUMINATION IMAGING AND NORMALIZED DIFFUSE EMISSION TRANSILLUMINATION IMAGING

(75) Inventor: Vasilis Ntziachristos, Larissa (GR)

(73) Assignee: The General Hospital Corporation, Boston, MA (US)

( * ) Notice: Subject to any disclaimer, the term of this patent is extended or adjusted under 35 U.S.C. 154(b) by 1327 days.

(21) Appl. No.: 12/973,075

(22) Filed: Dec. 20, 2010

(65) Prior Publication Data

US 2011/0087111 A1 Apr. 14, 2011

Related U.S. Application Data

(62) Division of application No. 11/720,967, filed as application No. PCT/US2005/044651 on Dec. 8, 2005, now abandoned.

(60) Provisional application No. 60/634,369, filed on Dec. 8, 2004.

(51) Int. Cl.
*A61B 6/00* (2006.01)
*A61B 1/00* (2006.01)
(Continued)

(52) U.S. Cl.
CPC ........... *A61B 1/00009* (2013.01); *A61B 5/0064* (2013.01); *A61B 5/0071* (2013.01); *A61B 5/0084* (2013.01); *A61B 5/0088* (2013.01); *A61B 5/415* (2013.01); *A61B 5/418* (2013.01); *A61B 1/043* (2013.01)

(58) Field of Classification Search
CPC ......... A61B 17/00; A61B 17/02; A61B 17/16
USPC .................................................. 600/476, 478
See application file for complete search history.

(56) References Cited

U.S. PATENT DOCUMENTS 5,347,374 A 9/1994 Fuss et al.
5,363,854 A 11/1994 Martens et al.
(Continued)

FOREIGN PATENT DOCUMENTS

EP 1 149 591 A2 10/2001
EP 1 477 103 A1 11/2004
(Continued)

OTHER PUBLICATIONS

Letter from Yuasa & Hara; dated Jul. 25, 2013; for JP Pat App. No. 2007-545669; 3 pages.
(Continued)

*Primary Examiner* — Joel F Brutus
(74) *Attorney, Agent, or Firm* — Fish & Richardson P.C.

(57) ABSTRACT

A system and method provide normalized fluorescence epi-illumination images and normalized fluorescence transillumination images. The normalization can be used to improve two-dimensional (planar) fluorescence epi-illumination images and two-dimensional (planar) fluorescence transillumination images. The system and method can also provide normalized bioluminescence epi-illumination images and normalized bioluminescence transillumination images. In some arrangements, the system and method can provide imaging of small animals, intro-operative imaging, endoscopic imaging, and/or imaging of hollow organs.

28 Claims, 13 Drawing Sheets

(51) Int. Cl.
　　　A61B 5/00　　　(2006.01)
　　　A61B 1/04　　　(2006.01)

(56) References Cited

U.S. PATENT DOCUMENTS

| | | | |
|---|---|---|---|
| 5,579,402 | A | 11/1996 | Hayen |
| 5,590,660 | A | 1/1997 | MacAuley et al. |
| 6,148,060 | A | 11/2000 | Collins et al. |
| 6,175,759 | B1 | 1/2001 | Chan et al. |
| 6,192,267 | B1 * | 2/2001 | Scherninski et al. ......... 600/473 |
| 6,343,228 | B1 | 1/2002 | Qu |
| 6,473,637 | B1 | 10/2002 | Hayashi |
| 6,615,063 | B1 | 9/2003 | Ntziachristos et al. |
| 6,763,148 | B1 | 7/2004 | Sternberg et al. |
| 6,821,245 | B2 | 11/2004 | Cline et al. |
| 6,899,675 | B2 | 5/2005 | Cline et al. |
| 8,078,265 | B2 | 12/2011 | Mahmood et al. |
| 2002/0103439 | A1 * | 8/2002 | Zeng et al. .................. 600/476 |
| 2003/0135092 | A1 | 7/2003 | Cline et al. |
| 2003/0158470 | A1 * | 8/2003 | Wolters et al. ............... 600/317 |
| 2003/0187319 | A1 | 10/2003 | Kaneko et al. |
| 2003/0232445 | A1 * | 12/2003 | Fulghum, Jr. ................... 436/63 |
| 2003/0236458 | A1 * | 12/2003 | Hochman .................. 600/431 |
| 2004/0109231 | A1 | 6/2004 | Haisch et al. |
| 2006/0082845 | A1 | 4/2006 | Watanabe |
| 2008/0015446 | A1 | 1/2008 | Mahmood et al. |
| 2008/0312540 | A1 | 12/2008 | Ntziachristos |
| 2012/0150043 | A1 | 6/2012 | Mahmood et al. |

FOREIGN PATENT DOCUMENTS

| | | |
|---|---|---|
| EP | 1 491 133 A1 | 12/2004 |
| EP | 1 637 062 A1 | 3/2006 |
| JP | 5-293108 | 11/1993 |
| JP | 8-89478 | 4/1996 |
| JP | HEI 9-294705 | 11/1997 |
| JP | 2001-299676 | 10/2001 |
| JP | 2002-301009 | 10/2002 |
| JP | 2003-290125 | 10/2003 |
| JP | 2003-290126 | 10/2003 |
| JP | 2004 321414 A | 11/2004 |
| JP | 2005-514147 | 5/2005 |
| WO | WO 95/26676 | 10/1995 |
| WO | WO 03/009739 A2 | 2/2003 |
| WO | WO 03/009739 A3 | 2/2003 |
| WO | WO 2006/063246 | 6/2006 |
| WO | WO 2008/008231 A2 | 1/2008 |

OTHER PUBLICATIONS

Japanese Final Office Action; recieved Jul. 25, 2013; for JP Pat App. No. 2007-545669; 5 pages.
EP Official Communication dated Oct. 4, 2012; for EP Pat. App. No. 05 853 540.2-2035; 3 pages.
U.S. Office Action dated Jul. 13, 2012; for U.S. Appl. No. 13/274,781; 8 pages.
Response to Office Action dated Jul. 13, 2012; for U.S. Appl. No. 13/247,781; 12 pages.
EP Official Communication dated Mar. 5, 2012; for EP Pat. App. No. 07 810 121.9; 3 pages.
Response to EP Official Communication dated Mar. 5, 2012; for EP Pat. App. No. 07 810 121,9; 2 pages.
Mamood et al.; Systems and Methods for Generating Fluorescent Light Images U.S. Appl. No. 13/274,781, filed Oct. 17, 2011; 74 pages.
EP Response to Official Communication dated Jun. 21, 2011; for EP Pat. App. No. 07801021.9; 22 pages.
European Office Action dated Aug. 7, 2013; for European Pat. App. No. 07 810 121.9; 5 pages.
Japanese Office Action; recieved Nov. 16, 2012; for JP Pat. App. No. 2007-545669; 6 pages.
EP Official Communication dated Jan. 13, 2011 from EP Pat. App. No. EP 07 810 121.9; 3 sheets.

U.S. Notice of Allowance dated Jul. 22, 2011 for U.S. Appl. No. 11/456,625; 6 sheets.
Response filed Sep. 16, 2009; to Office Action dated Apr. 16, 2009; for U.S. Appl. No. 11/456,625; 21 pages.
European Office Action; dated Oct. 4, 2012; for EP Pat. App. No. 05 853 540.2; 3 sheets.
Letter from Yuasa & Hara; dated Jul. 19, 2013; for JP Pat. App. No. 2009-519457; 6 pages.
Japanese Notice of Rejection; dated May 30, 2013; for JP Pat. App. No. 2009-519457; 2 pages.
Letter from Yuasa & Hara; dated Jul. 19, 2013; for JP Pat. App. No. 2013-011066; 8 pages.
Japanese Notice of Rejection; dated May 30, 2013; for JP Pat. App. No. 2013-011066; 1 pages.
Letter from Yuasa & Hara; dated Jul. 19, 2013; for JP Pat. App. No. 2013-011068; 5 pages.
Japanese Notice of Rejection; dated May 30, 2013; for JP Pat. App. No. 2013-011068; 1 pages.
Office Action Restriction Requirementdated Dec. 14, 2009 for U.S. Appl. No. 11/720,967; 5 pages.
Response to Office Action Restriction Requirement dated Dec. 14, 2009 for U.S. Appl. No. 11/720,967; 1 page.
Office Action dated Sep. 20, 2010 for U.S. Appl. No. 11/720,967; 13 pages
PCT Preliminary Report on Patentability and Written Opinion dated Jun. 21, 2007 for PCT Pat. App. PCT/US2007/044651.
EP Official Communication dated Jan. 13, 2011 for EP Pat. App. No. 07810121.9-2319.
Office Action Restriction Requirement dated Mar. 6, 2009 for U.S. Appl. No. 11/456,625; 10 pages.
Response to Office Action Restriction Requirement dated Mar. 6, 2009 for U.S. Appl. No. 11/456,625; 1 page.
Office Action dated Apr. 16, 2009 for U.S. Appl. No. 11/456,625.
Office Action dated Apr. 16, 2009 for U.S. Appl. No. 11/456,625; 21 pages.
Office Action dated Mar. 24, 2011 for U.S. Pat. App. No. MGH-076PUS, filed on Jul. 11, 2006; 9 pages.
Response to Office Action dated Mar. 24, 2011 for U.S. Pat. App. No. MGH-076PUS, filed on Jul. 11, 2006; 12 pages.
PCT Partial Search Report dated Dec. 13, 2006 for PCT Pat. App. No. PCT/US2007/015295; 5 pages.
Letter from Yuasa and Hara; dated Jan. 16, 2013; for Japanese Patent Application No. 2009-519457; 3 pages.
Letter to Yuasa and Hara; dated Jan. 21, 2013; for Japanese Patent Application No. 2009-519457; 2 pages.
Letter from Yuasa and Hara; dated Feb. 20, 2013; for Japanese Patent Application No. 2009-519457; 9 pages.
Letter to Yuasa and Hare; dated Mar. 21, 2013; with instructions for Response to Japanese Office Action; for Japanese Pat. App. No. 2007-545669; 10 pages.
Letter from Yuasa and Hara; dated Apr. 19, 2013; regarding Response to Japanese Office Action; for Japanese Pat. App. No. 2007-545669; 1 page.
Response to Japanese Office Action; filed on Mar. 26, 2013; for Japanese Pat. App. No. 2007-545669; 6 pages.
Response to European Office Action; filed Apr. 12, 2013; for European Pat. App. No. 05853540.2; 31 pages.
EP Response to Official Communication dated Jun. 28, 2011; for EP Pat. App. No. 07810121.9; 22 pages.
Funovics et al.; "Catheter-based in Vivo Imaging of Enzyme Activity and Gene Expression: Feasibility Study in Mice;" Center for Molecular Imaging Research, Massachusetts General Hospital; Radiology, Molecular Imaging, Jun. 2004; pp. 659-666.
Funovics et al.; "Miniaturized Multichannel Near Infrared Endoscope for Mouse Imaging;" 2003 Massachusetts Institute of Technology; Molecular Imaging; vol. 2, No. 4; Oct. 2003; pp. 350-357.
Kircher et al.; "A Dual Fluorochrome Probe for Imaging Proteases;" 2004 American Chemical Society; Bioconjugate Chem.; American Chemical Society; vol. 15, No. 2; Feb. 28, 2004; pp. 242-248.

(56) References Cited

OTHER PUBLICATIONS

Mahmood et al.; "Feasibility of in Vivo Multichannel Optical Imaging of Gene Expression: Experimental Study in Mice;" Center for Molecular Imaging Research, Massachusetts General Hospital; Radiology; vol. 224, No. 2; Aug. 2002; pp. 446-451.
Mahmood et al.; "Near-Infrared Optical Imaging for Protease Activity for Tumor Detection;" Department of Radiology, Center for Mulocular Imaging Research, Massachusetts General Hospital; Radiiology; vol. 213, No. 3; Dec. 1999; pp. 866-760.
Weissleder et al.; "In Vivo Imaging of Tumors with Protease-Activated Near-Infrared Fluorescent Probes;" 1999 Nature America Inc.; Nature Biotechnology; vol. 17, Apr. 1999; pp. 375-378.
PCT Search Report and Written Opinion of the ISA for PCT/US2005/044651 dated Apr. 4, 2006.
PCT International Preliminary Report on Patentability of the ISA for PCT/US2005/044651 dated Jun. 21, 2007.
PCT Search Report and Written Opinion of the ISA for PCT/US2007/015295 dated Apr. 4, 2008.
PCT International Preliminary Report on Patentability of the ISA for PCT/US2007/015295 dated Jan. 22, 2009.
U.S. Appl. No. 11/720,967; 405 pages.
Transmittal of Japanese Notice of Rejection; dated Oct. 25, 2012; for JP Pat. App. No. 2009-519457; 4 sheets.
Notice of Allowance; dated Dec. 10, 2012; for U.S. Appl. No. 13/274,781; 10 sheets.
Letter to Yuasa and Hara dated Dec. 3, 2013; for Japanese Pat. App. No. 2007-545669; 12 pages.
Letter from Yuasa and Hasa dated Dec. 20, 2013; for Japanese Pat. App. No. 2007-545669; 1 page.
Japanese Argument and Amendment filed Dec. 6, 2013; for Japanese Pat. App. No. 2007-545669; 6 pages.
Japanese Claims (English Translation) filed on Dec. 6, 2013; for Japanese Pat. App. No. 2007-545669; 4 pages.
Japanese Office Action recieved Apr. 25, 2014; for Japanese Pat. App. No. 2007-545669; 1 page.
European Office Action dated Mar. 24, 2014; for European Pat. App. No. 05 853 540.2; 4 pages.
European Response to Office Action filed Oct. 3, 2014; for European Pat. App. No. 05853540.2; 15 pages.
European Office Action dated Jan. 30, 2015; for EP Pat. App. No. 05 853 540.2; 4 pages.

\* cited by examiner

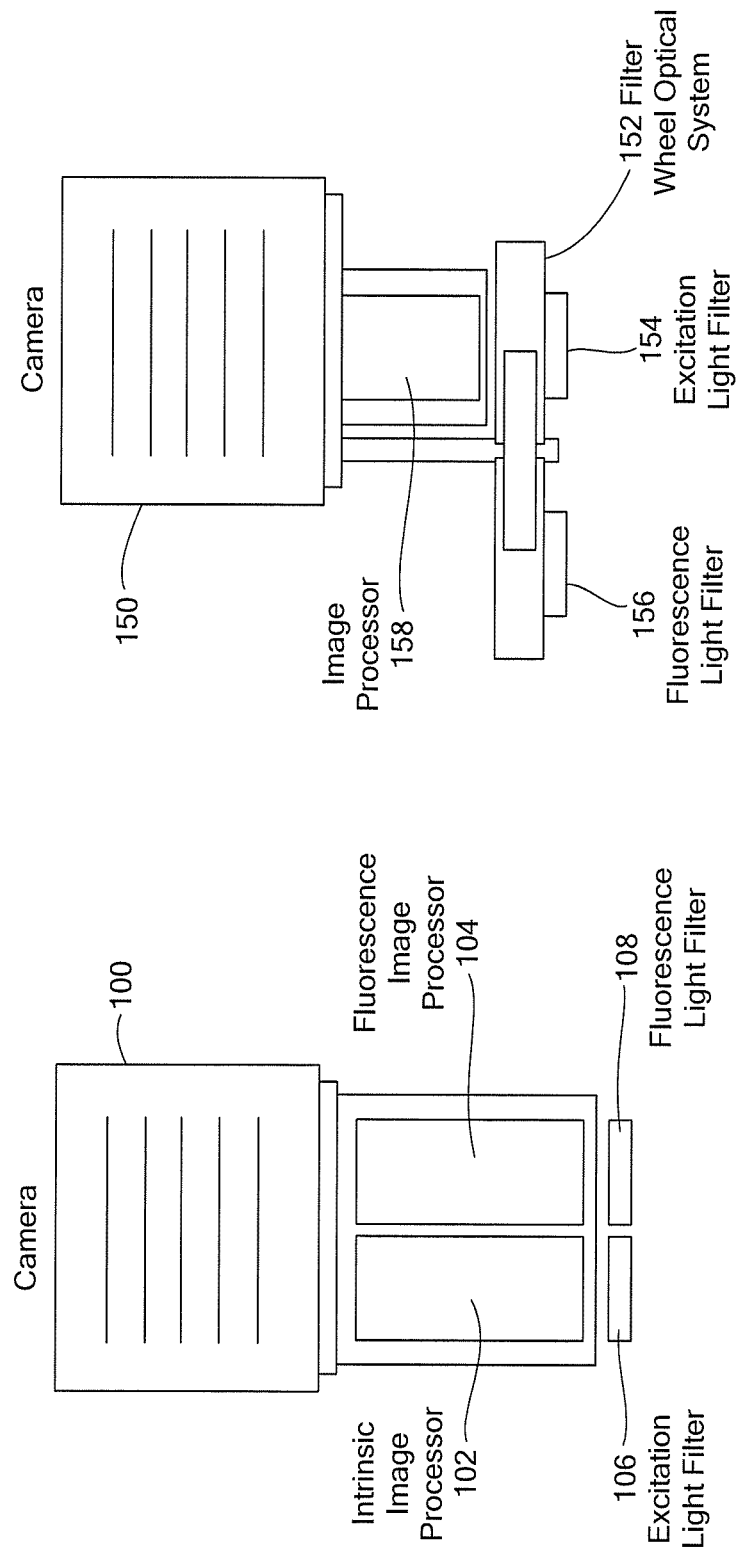

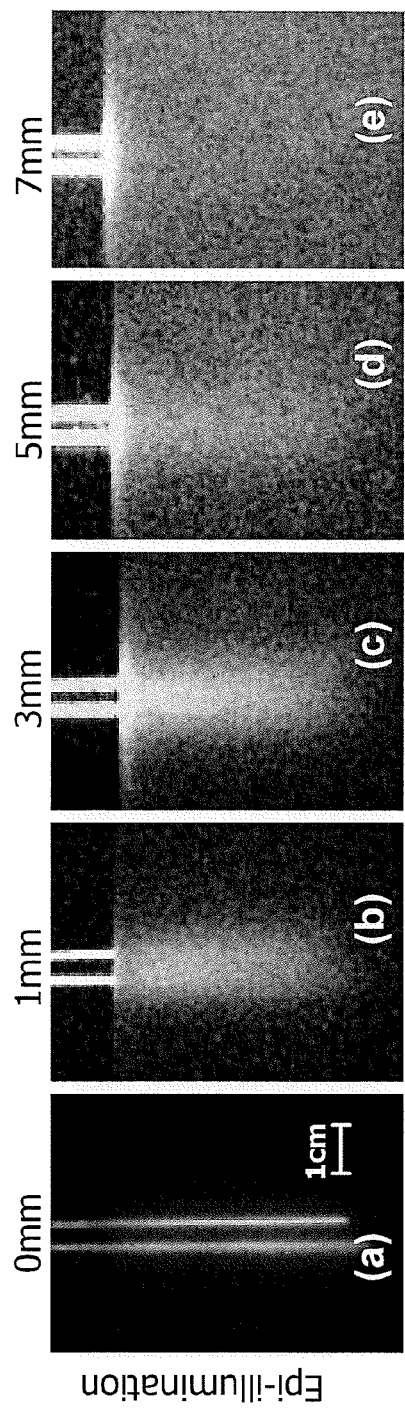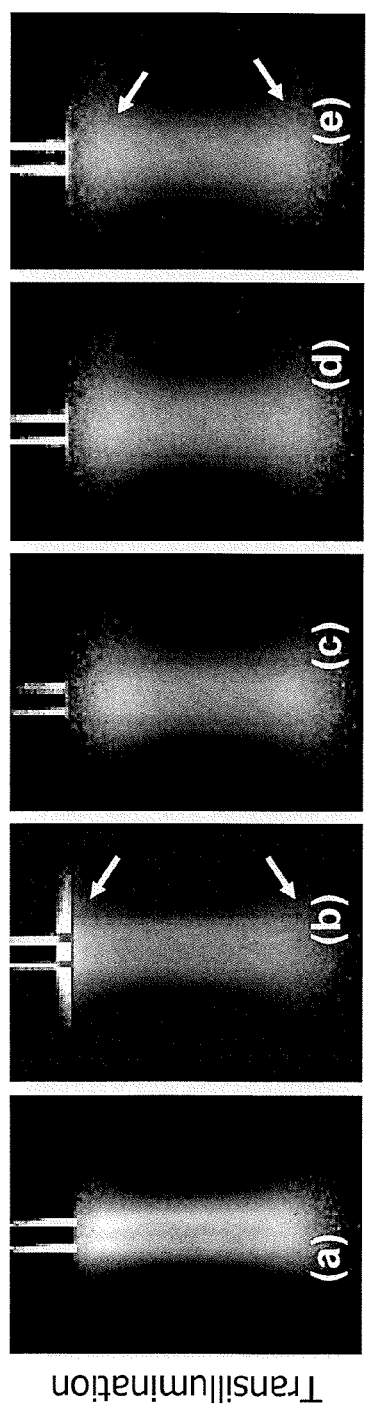

SYSTEM AND METHOD FOR NORMALIZED DIFFUSE EMISSION EPI-ILLUMINATION IMAGING AND NORMALIZED DIFFUSE EMISSION TRANSILLUMINATION IMAGING

CROSS REFERENCE TO RELATED APPLICATIONS

This application is a Divisional Application of and claims the benefit of U.S. patent application Ser. No. 11/720,967 filed on Jun. 6, 2007, which is a U.S. National Stage application under 35 U.S.C. §371 of, and claims the benefit of, International Patent Application No. PCT/US2005/044651 filed on Dec. 8, 2005, all of which applications claim priority to U.S. Provisional Patent Application No. 60/634,369 filed on Dec. 8, 2004, all of which applications are hereby incorporated herein by reference in their entirety.

FIELD OF THE INVENTION

This invention relates generally to medical imaging and, more particularly, to a system and method for generating fluorescence epi-illumination images, fluorescence transillumination images, and bioluminescence images associated with small animal imaging, intra-operative imaging, endoscopic imaging and imaging of hollow organs.

BACKGROUND OF THE INVENTION

Fluorescence images can be generated in-vivo for imaging of molecular functions and gene expression in live biological tissues. Fluorescence imaging of small animals has been used in biological research, including research in drug discovery and in investigation of fluorescent reporter technologies. Fluorescence imaging has also been used to study various human tissues, for example, tissues exhibiting epithelial diseases, the human breast, joints, and human teeth.

Conventionally, fluorescent light has been used for high-resolution imaging of histological slices of biological tissue using so-called fluorescence microscopy. Fluorescence microscopy is used to provide relatively high-resolution images. However, tissue sectioning used in conventional fluorescence microscopy is limited to slice thicknesses (i.e., tissue depths) on the order of half a millimeter, and therefore, conventional fluorescence microscopy is not appropriate for imaging through entire organs or through the whole human body.

In order to provide images a bit deeper into tissue, conventional systems and techniques have used light sources and fluorochromes that emit near infrared light. The near infrared light is selected because near infrared light has low absorption and can penetrate several centimeters into biological tissue. Near infrared light is used in a variety of optical imaging systems and techniques.

Fluorescent light can be emitted from a tissue in response to an excitation light source transmitting excitation light into the tissue. The excitation light excites the emission of fluorescent light from fluorochromes within the tissue.

Similarly, bioluminescence imaging has been used to image into tissues. The difference between fluorescence and bioluminescence imaging is that, for bioluminescence imaging, no excitation light source is required to cause emission of bioluminescent light. Emission of bioluminescent light in bioluminescence imaging is caused by a chemi-luminescent reaction within the tissue, resulting from transgenes.

The most common macroscopic technique that is conventionally used for fluorescence imaging is fluorescence reflectance imaging (FRI), which is also referred to herein as fluorescence epi-illumination imaging (FEI).

Epi-illumination light sources and epi-illumination imaging are further described below. In general, an epi-illumination light source generates light that is directed toward and then reflects from a surface of biological tissue and/or that propagates into the biological tissue and reflects from internal structures and/or surfaces of the biological tissue. To form an epi-illumination image, image light is collected generally on the same side of the tissue as the epi-illumination light source.

An FEI system transmits light onto and/or into biological tissue and collects the fluorescence light that is emitted back from the tissue, including light that is emitted back from within the tissue. In fluorescence epi-illumination imaging, excitation light (for example, near-infrared light) from an epi-illumination light source is used to illuminate the tissue. The epi-illumination light source is used to excite fluorochromes within the tissue that, in turn, emit fluorescent light. In some arrangements, the emitted light is visible light. In other arrangements, the emitted light is near infra red light. The emitted light can be visually inspected or it can be captured with a CCD camera or other photon detector positioned generally on the same side of the tissue as the epi-illumination light source. Bioluminescence imaging can be similar to fluorescent epi-illumination imaging, but bioluminescence is generated without an epi-illumination light source.

As described above, conventional fluorescence imaging with near-infrared light provides images having relatively low resolution and only small penetration (2-3 mm) of tissue. Higher resolution is achieved when spectral information is utilized and "umixed."

A second method, which has not yet been utilized for research using small animals, but which has found applications in optical breast imaging, uses a transillumination light source to generate transillumination images. Similar to the above-described epi-illumination light source, a transillumination light source generates light that propagates into the tissue. However, unlike epi-illumination light, the transillumination light propagates entirely through the tissue. In transillumination imaging, image light is collected generally on the opposite side of the tissue from the transillumination light source.

Similar to that described above for fluorescence epi-illumination imaging, in fluorescence transillumination imaging, excitation light (for example, near infra red light) from a transillumination light source is used to illuminate a tissue. The excitation light propagates into the tissue, exciting the emission of fluorescent light from within the tissue. However, in contrast to the above-described fluorescence epi-illumination arrangement, in fluorescence transillumination imaging, a CCD camera or other photon detector is positioned generally on the opposite side of the tissue from the transillumination light source. In some arrangements, the emitted light is near infrared light. Fluorescence transillumination imaging (FTI) has been used to visualize functional characteristics of cardiac muscle and in dental diagnostic practice.

In some transillumination arrangements, the transillumination light source and the light detector lie on a virtual line passing through the tissue. In some arrangements the virtual line is generally perpendicular to the tissue and, in other arrangements, the virtual line is not generally perpendicular to the tissue.

Fluorescence epi-illumination imaging (FEI), fluorescence transillumination imaging (FTI), and bioluminescence imaging (BI) are forms of "planar" imaging, which provide two-dimensional images.

More advanced optical imaging systems and methods have been developed, which utilize tomographic methods. These systems and methods operate by obtaining photonic measurements at different projections (i.e., angles) to the tissue and combining the measurements using a tomographic algorithm. Tomography can provide a more accurate image than the above-described forms of planar imaging. Advantages of tomography include an ability for image quantification, an ability to provide two-dimensional or three-dimensional images, an ability to provide three-dimensional imaging with feature depth measurements, and higher sensitivity and higher resolution as compared to planar imaging. In some applications, tomography has been used in-vivo to measure enzyme regulation and treatment response to drugs. In these applications, tomography provides superior imaging performance to planar imaging. However, tomography is more complex than planar imaging, requiring more advanced instrumentation, requiring multiple illumination points (projections), which can require multiple light sources, and requiring advanced theoretical methods for modeling photon propagation in tissues.

SUMMARY OF THE INVENTION

The system and method for normalized epi-illumination imaging and normalized transillumination imaging provide normalization of images generated by planar fluorescence epi-illumination imaging, by planar fluorescence transillumination imaging, by planar bioluminescence epi-illumination imaging, and by planar bioluminescence transillumination imaging. The normalization results in substantially improved images. As further described below, by using a combination of normalized epi-illumination images and normalized transillumination images, each having particular imaging characteristics, still further improvement can be achieved.

In some particular arrangements, as further described below, the system and method can be used during surgery to identify tumors or other lesions and borders thereof. In other words, the system and method can be used for intra-operative imaging. In some arrangements, the system and method can also be used for fluorescence endoscopy and/or laparoscopy. In some arrangements, the system and method can also be used in oral and dental procedures to provide oral or dental images.

In accordance with the present invention, a method of imaging includes generating incident light including excitation light with an excitation light source and directing the incident light toward a tissue. The method also includes receiving the incident light with a light detector after the incident light has interacted with a tissue. The method further includes receiving emitted light with the light detector, wherein the emitted light is emitted from the tissue. The method further includes generating an intrinsic image of the tissue in response to the incident light. The method further includes generating an un-normalized emitted light image of the tissue. The method further includes combining the un-normalized emitted light image and the intrinsic image to generate a normalized emitted light image of the tissue.

The normalized emitted light image generated by the method is a normalized fluorescence epi-illumination image, a normalized fluorescence transillumination image, a normalized bioluminescence epi-illumination image, and/or a normalized bioluminescence transillumination image.

In accordance with another aspect of the present invention, a system for imaging a tissue includes an excitation light source adapted to generate incident light including excitation light. The system also includes a light receiver adapted to receive the incident light after the incident light has interacted with a tissue, further adapted to receive emitted light, wherein the emitted light is emitted from the tissue, further adapted to generate an intrinsic image of the tissue in response to the incident light, and further adapted to generate an un-normalized emitted light image of the tissue. The system further includes a normalization processor adapted to combine the un-normalized emitted light image and the intrinsic image to generate a normalized emitted light image associated with the tissue.

The normalized emitted light image generated by the system is a normalized fluorescence epi-illumination image, a normalized fluorescence transillumination image, a normalized bioluminescence epi-illumination image, and/or a normalized bioluminescence transillumination image.

BRIEF DESCRIPTION OF THE DRAWINGS

The foregoing features of the invention, as well as the invention itself may be more fully understood from the following detailed description of the drawings, in which:

FIG. 2 is a pictorial showing greater detail of a light detector that can be used in the normalized fluorescence epi-illumination imaging and normalized fluorescence transillumination imaging systems of FIGS. 1 and 1B;

FIG. 2A is a pictorial showing greater detail of another light detector that can be used in the normalized fluorescence epi-illumination imaging and normalized fluorescence transillumination imaging systems of FIGS. 1 and 1B;

FIG. 3 is a series of images of a phantom, generated by the systems of FIGS. 1 and 1B, when used for normalized fluorescence epi-illumination imaging;

FIG. 3A is a series of images of the phantom, also seen in FIG. 3, provided by the systems of FIGS. 1 and 1B when used for normalized fluorescence transillumination imaging;

FIG. 5A is another series of images of another phantom, showing an intrinsic epi-illumination image at the excitation light wavelength, a fluorescence epi-illumination image, and a normalized fluorescence epi-illumination image;

FIG. 5B is a series of images of the phantom, also seen in FIG. 5, showing an intrinsic transillumination image at the excitation light wavelength, a fluorescence transillumination image, and a normalized fluorescence transillumination image;

FIG. 5C is another series of images of the phantom, also seen in FIG. 5A, showing an intrinsic transillumination image at the excitation light wavelength, a fluorescence transillumination image, and a normalized fluorescence transillumination image;

DETAILED DESCRIPTION OF THE INVENTION

Figure 1:
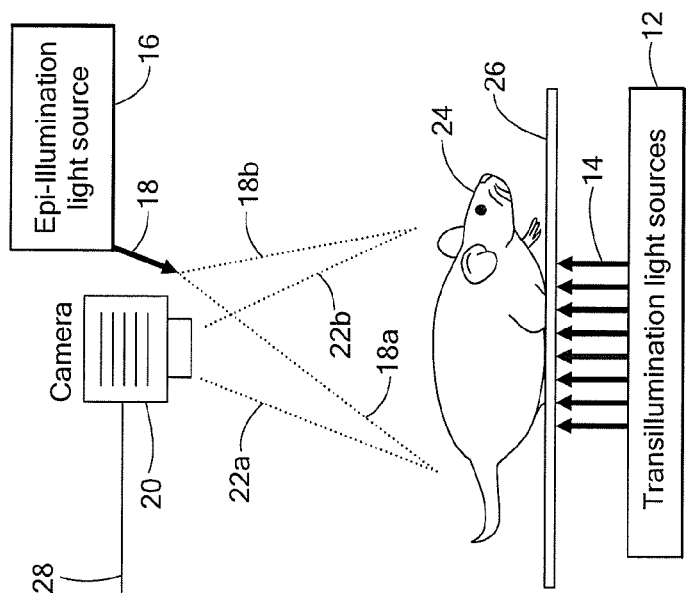
FIG. 1 is a pictorial of system used for normalized fluorescence epi-illumination imaging and normalized fluorescence transillumination imaging having a normalization processor.

Before describing the imaging system and method, some introductory concepts and terminology are explained. As used herein, the term "phantom" is used to describe a test object being imaged. A phantom is typically an article having diffuse light propagation characteristics similar to living tissue, for example, a piece of appropriately engineered resin block. For another example, a phantom can be a vial, which contains cells having fluorescent proteins therein, i.e. a fluorescent marker or a fluorochrome.

As used herein, the term "excitation light" is used to describe light generated by an "excitation light source" that is incident upon a biological tissue. The excitation light can interact with the tissue, and can be received by a light detector (e.g., a camera), at the same wavelength (excitation wavelength) as that at which it was transmitted by the excitation light source. The excitation light can be monochromatic, or it can cover a broader spectrum, for example, white light. The excitation light can be used to generate a so-called "intrinsic excitation light image" of the tissue (or more simply, and intrinsic image), i.e., an image obtained at the same wavelength as the wavelength of the excitation light. The excitation light can also be used to excite fluorescence within the tissue, and to generate a so-called "fluorescence image" of the tissue, at a selected different wavelength than the wavelength of the excitation light.

As used herein, the term "incident light" is used to more generally describe light that is generated by the excitation light source, wherein the incident light can include not only the excitation light having a wavelength selected to excite fluorescence, but also light having other wavelengths. The incident light can include only the excitation light, or it can also include other wavelengths. The wavelengths of the incident light can be generated simultaneously or at different times. The incident light can be used to generate a so-called "intrinsic incident light image" of the tissue (or more simply, an intrinsic image). The intrinsic incident light image is either an image obtained at the same wavelength as the wavelength of the excitation light (i.e., an intrinsic excitation light image), an image obtained at a different wavelength than the wavelength of the excitation light, or an image obtained by a combination of images obtained at a variety of wavelengths, which may or may not include the wavelength of the excitation light. The combination of images is further described below.

In general, it will be understood that an intrinsic image is an image of natural structures inside the tissue, exclusive of any fluorescence of the tissue or of fluorescence generated by fluorescence markers within the tissue. In contrast, a fluorescence image is an image of only the tissue fluorescence or of fluorescence generated by the fluorescence markers within the tissue. The intrinsic image can be either an intrinsic excitation light image, or, more generally, an intrinsic incident light image.

As used herein, the term "epi-illumination light source" is used to describe an excitation light source that can generate a form of excitation light (also referred to herein as "epi-illumination light") that reflects from a surface of biological tissue and/or that propagates into the biological tissue, in order to form a so-called "epi-illumination image." To form an epi-illumination image, image light is collected generally on the same side of the tissue as the epi-illumination light source. An epi-illumination image can be either an intrinsic epi-illumination image (no fluorescence) or a fluorescence epi-illumination image (only fluorescence).

As used herein, the term "transillumination light source" is used to describe an excitation light source that can generate a form of excitation light (also referred to herein as "transillumination light") that propagates into the tissue, in order to generate a so-called "transillumination image." To form a transillumination image, light is collected generally on the opposite side of the tissue from the transillumination light source. Like an epi-illumination image, a transillumination image can be either an intrinsic transillumination image (no fluorescence) or a fluorescence transillumination image (only fluorescence).

In some arrangements, the epi-illumination light source and/or the transillumination light source(s) can, more generally, generate incident light, which includes the excitation light.

To generate an intrinsic epi-illumination image, the excitation light (epi-illumination light) is received by a camera after being directed back from (e.g., reflected from) an object being imaged. In contrast, to generate an intrinsic transillumination image, the excitation light (transillumination light) is be received by a camera after it passes through the object being imaged.

Similarly, to generate a fluorescence epi-illumination image, the excitation light (epi-illumination light) excites fluorescence on or in the tissue, which is directed back from tissue being imaged, and which is received at a wavelength different from the excitation light. To generate a fluorescence transillumination image, the excitation light (transillumination light) also excites fluorescence in the tissue, which is directed through the tissue being imaged, and which is received at a wavelength different from the excitation light.

As used herein, the term "emitted light" is used to describe light generated by or within a biological tissue. As used herein, the term "fluorescence" is used to describe a form of emitted light generated via excitation of a marker fluorochrome in response to the excitation light. As used herein, the term "bioluminescence" is used to describe another form of emitted light emitted from a tissue, generally in the absence of the excitation light. As used herein, the term "emitted light image" is used to describe either a fluorescence image or a bioluminescence image.

As used herein, the term "image" is used to describe a visual presentation of something such as an object or a scene. An image may be represented as image data, which can be displayed on a computer monitor. Image data can be generated by a digital camera or other image device and provided to a computer system or other processing device. However, it will be understood that the term "image," as used herein, is also used to refer to the image data.

The system and method described herein to explain inventive concepts refer to the use of particular types of light or light having particular characteristics. For example, reference is made to systems and methods using near-infrared excitation light, which provides particular benefits in the near-infrared (NIR) wavelength range of about 650-1000 nm. It should, however, also be appreciate that the system and method described herein can also be applied to excitation light having other wavelengths, for example to light in the visible range of about 400 nm-650 nm. Also, the system and method apply to a system in which excitation light is generated by an excitation light source in one wavelength range, for example, in the visible range, and the fluorescent light emitted by fluorochromes is in another wavelength range, for example in the NIR range. The system and method also apply where both the excitation light generated by the excitation light source and the light emitted by the fluorochromes are in the NIR range. In addition, excitation light and/or emitted light having a wavelength at the interface of visible range and near-infrared range can be used, for example in the 550 nm-650 nm range. Some wavelengths are particularly beneficial for bioluminescence imaging and for imaging of red-shifted fluorochromes and fluorescent proteins. The excitation light can have the same intensity at all wavelengths therein, or it can have predetermined attenuation of selected wavelengths, e.g., by using appropriate filters. Also, excitation light beyond the wavelength range of 400 nm to 1000 nm can be used.

The term "fluorochrome" as used herein will be understood to describe a type of known biocompatible dye or other fluorescence agent that can be systemically or topically applied to a biological tissue. Some fluorochromes are target fluorochromes, which tend to congregate at certain anatomical, functional, or molecular features in the tissue, including for example, at cancerous lesions.

Referring now to FIG. 1, an imaging system 10 includes a plurality of transillumination light sources 12 adapted to generate excitation (transillumination) light, which is represented by a plurality of arrows 14. The system 10 also includes an epi-illumination light source 16 adapted to generate excitation (epi-illumination) light represented by an arrow 18 and lines 18a, 18b, which are generally indicative of light beam boundaries. Thus, the epi-illumination light source 16 emits a single relatively broad beam of light 18, 18a, 18b. The transillumination light 14 and the epi-illumination light 18, 18a, 18b are directed toward a biological tissue 24. In this particular example, the biological tissue is shown to be a mouse 24.

In some embodiments, an optional light mask 26 can be disposed between the transillumination light sources 12 and the biological tissue 24. Thus, in those embodiments, which utilize a light mask such as light mask 26, the transillumination light 14 passes through the light mask 26, and impinges upon the biological tissue 24. The light mask is further described below in greater detail in conjunction with FIG. 1A.

The system 10 also includes a camera 20 (or other type of detector) adapted to receive light represented by lines 22a, 22b, which lines are generally indicative of light beam boundaries. As further described below, the light 22a, 22b is associated with the transillumination light sources 12 and/or with the epi-illumination light source 16. The camera 20 generates image information 28, which is received by a normalization processor 30. The normalization processor 30 generates normalized image information 32, which is received by and displayed by a display 34. The normalization processor 30 is further described below, where it will become apparent that the normalization provided by the normalization processor 30 results in improved "normalized" fluorescence images of a subject 24.

In operation, the camera 16 receives the light 26a, 26b. In some embodiments, the transillumination light sources 18 and the epi-illumination light source 16 generate excitation light, 18, 20, respectively, concurrently and the camera 16 receives light 26a, 26b having contributions from both the transillumination light sources 12 and the epi-illumination light source 16 at the same wavelength as each of the excitation light sources 12, 16. In other embodiments, the transillumination light sources 12 and the epi-illumination light source 16 generate the excitation light 18, 20, respectively, at different times, so that at any particular time the camera 16 receives the light 26a, 26b from one of the transillumination light sources 12 and the epi-illumination light source 16.

The light 26a, 26b received by the camera 16 in response to the excitation light 18, 18a, 18b generated by the epi-illumination light source 16 can have contributions from the excitation light 18, 18a, 18b at the excitation light wavelength and also contributions from emitted light (fluorescence or bioluminescence), emitted within the subject 24 at a different wavelength in response to the excitation light 18, 18a, 18b. Contributions from the excitation light 18, 18a, 18b can be used to form an intrinsic epi-illumination image, and contributions from the resulting emitted fluorescent light can be used to form a fluorescence epi-illumination image and also a normalized fluorescence epi-illumination image.

Similarly, the light 26a, 26b received by the camera 16 in response to the excitation light 14 generated by the transillumination light source 12 can have contributions from the excitation light 14 at the excitation light wavelength and contributions from emitted light (fluorescence or bioluminescence), emitted within the subject 24 at a different wavelength in response to the excitation light 14. Contributions from the excitation light 14 can be used to form an intrinsic transillumination image, and contributions from the emitted light can be used to form a fluorescence transillumination image and also a normalized fluorescence transillumination.

From the above discussion, it should be recognized that the system 10 can generate normalized fluorescence epi-illumination images, normalized fluorescence transillumination images, or both normalized fluorescence epi-illumination images and normalized fluorescence transillumination images. The system 10 can also generate normalized bioluminescence images.

As described above, normalized fluorescence epi-illumination images can be generated by illuminating tissue (e.g. the mouse 24 in FIG. 1) with the excitation light 18, 18a, 18b generated by the epi-illumination light source 16. The camera 20, positioned on the same side of the tissue 24 as the epi-illumination light source 16, is used to capture both excitation (epi-illumination) light reflected from the tissue 24 to form an intrinsic epi-illumination image, and fluorescent light, which is emitted from within the tissue 24 in response to the excitation (epi-illumination) light 18, 18a, 18b to form an un-normalized fluorescence epi-illumination image. The intrinsic epi-illumination image and the un-normalized fluorescence epi-illumination image are combined by the normalization processor 30 to generate the normalized fluorescence epi-illumination image.

Also as described above, normalized fluorescence transillumination images can be generated by illuminating the tissue (here the mouse 24) with the excitation light 14 generated by the transillumination light sources 12. The camera 20, positioned on the opposite side of the tissue 24 as the transillumination light sources 12, is used to capture both excitation (transillumination) light passing through the tissue 24 to generate an intrinsic transillumination image, and fluorescent light, which is emitted from within the tissue 24 in response to the excitation (transillumination) light 14 to form an un-normalized fluorescence transillumination image. The intrinsic transillumination image and the un-normalized fluorescence transillumination image are combined by the normalization processor 30 to generate the normalized fluorescence transillumination image.

To generate normalized bioluminescence images, the system 10 collects an un-normalized image of bioluminescence light. In this case, bioluminescence light is spontaneously emitted and is not generated in response to the excitation lights 14, 18, 18a, 18b. The un-normalized bioluminescence image can be combined by the normalization processor 30 with either the intrinsic epi-illumination image or with the intrinsic transillumination image to generate the normalized bioluminescence image.

For either epi-illumination imaging or transillumination imaging, in order to form the intrinsic images in some embodiments, the excitation light source generates one or more wavelengths (i.e. incident light) including, but not limited to, a wavelength of excitation light, and the intrinsic image is generated by combining intrinsic images associated with the one or more wavelengths. In some arrangements the combination is a weighted average.

While the term "excitation light" is described above to be associated with light that can excite fluorescence in biological tissue, the excitation light can also be used by the system 10 in order to generate the normalized bioluminescence images. In some arrangements, the excitation light can be generated at the bioluminescence wavelengths so that it can be used to capture the propagation characteristics of the bioluminescence in the tissue. For example, as described above, in normalized bioluminescence transillumination imaging, the system 10 collects both an image of the excitation (transillumination) light (intrinsic image) and an un-normalized image of bioluminescence light.

As described above, normalized fluorescence transillumination imaging is provided by positioning the plurality of transillumination light sources 12 generally on the other side of the tissue 24 from the camera 20. The transillumination light sources 12 can have an illumination pattern, for example, by using an array of transillumination light sources 12 disposed in a predetermined pattern, or by using an optical guiding system disposed in the predetermined pattern, for example, the light mask 26

In fluorescence transillumination imaging using the plurality of transillumination light sources 12, transillumination imaging can be accomplished by a superposition of light signals associated with excitation light generated by each one of the plurality of transillumination light sources 12. In essence, each one of the transillumination light sources 12 can be sequentially illuminated and resulting intrinsic and fluorescence images can be sequentially captured.

The camera 20 can collect both excitation light associated with the light sources 12, 16, which is reflected from and/or which passed through the tissue 24, and can collect emitted light associated with a fluorochrome within the tissue and/or associated with an endogenous tissue fluorescent molecule. The system 10 can also collect emitted bioluminescence light, for example, when the excitation light sources 12, 16 are turned off. The same system 10, using the same camera 20, can be used to generate both normalized fluorescence epi-illumination images and normalized fluorescence transillumination images. The camera 20 is shown in greater detail in conjunction with FIGS. 2 and 2A.

While it is described above that the epi-illumination light source 16 and the transillumination light sources 12 are adapted to generate excitation light, in other arrangements, the epi-illumination light source 16 and/or the transillumination light sources 12 are adapted to generate incident light having the wavelength of the excitation light and also other wavelengths.

Figure 1A:
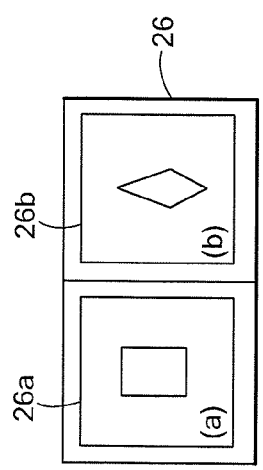
FIG. 1A is a pictorial showing two light masks that can be used in conjunction with light sources of FIG. 1.

Referring now to FIG. 1A which is comprised of a first panel labeled "(a)" and a second panel labeled "(b)", a first exemplary light mask 26a shown in the panel (a) and a second exemplary light mask 26b shown in the panel (b). The masks 26a, 26b serve to block stray light and also excitation light that could otherwise directly hit the camera (or other detector) and saturate it or damage it. Additional absorbing materials can be used to selectively prevent excitation light 14, 18 generated by the excitation light sources 12, 16, respectively, from directly entering the camera 20. In other arrangements, selective beam-scan patterns can be used to avoid direct exposure of the camera 20 to excitation light 14, 18. In other arrangements, adaptive attenuation of light intensity from the plurality of transillumination light sources 12 can be used to prevent saturation of the camera 20 and also to improve the dynamic range of images acquired by the camera 20. For example, dynamic range can be improved for light that is minimally attenuated by tissue, for example, light close to the tissue borders.

Figure 1B:
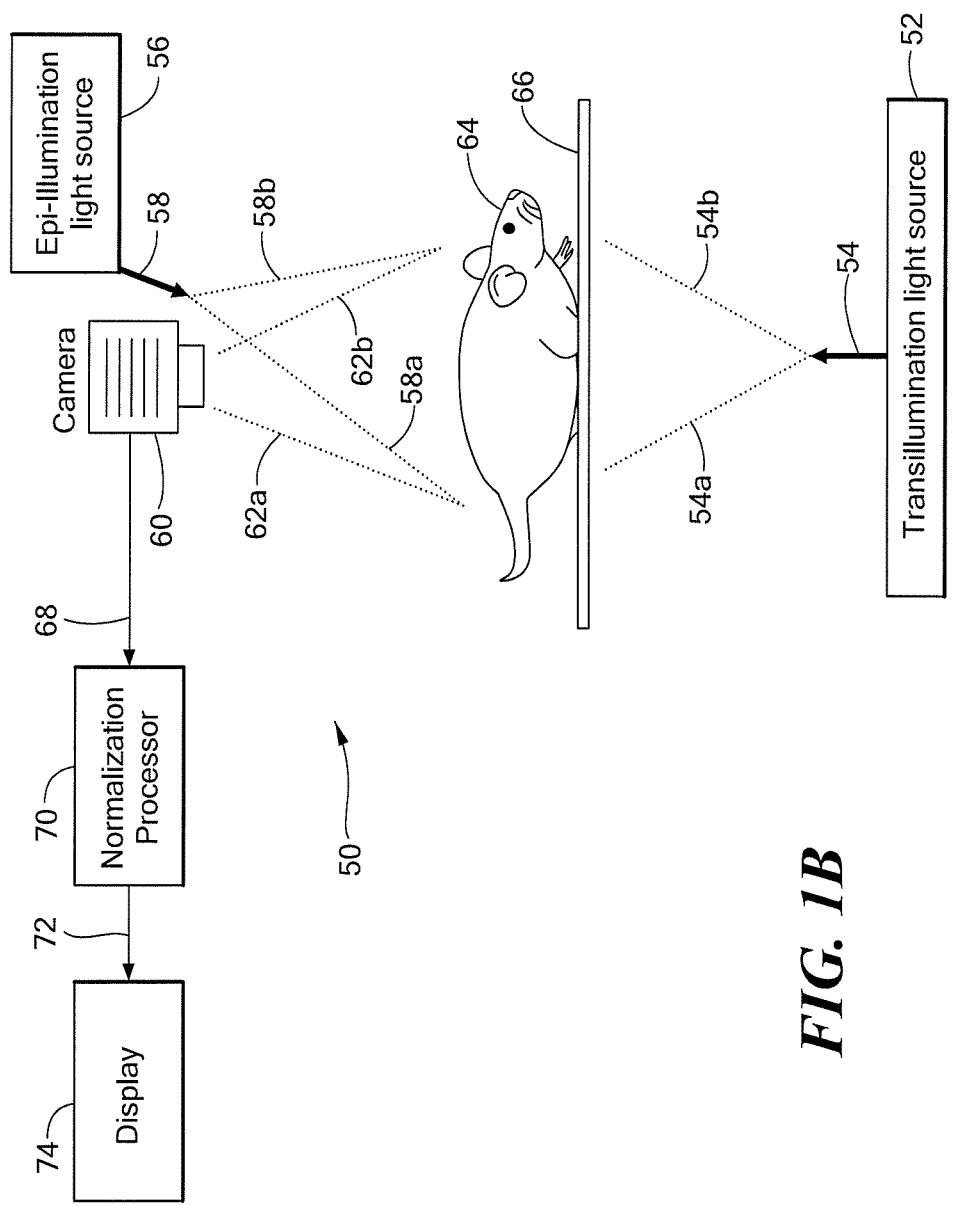
FIG. 1B is a pictorial of another system used for normalized fluorescence epi-illumination imaging and normalized fluorescence transillumination imaging having another normalization processor.

Referring now to FIG. 1B, another system 50, which is similar to the system 10 of FIG. 1, but which includes a single transillumination light source 52 having a relatively wide beam of excitation light, represented by an arrow 54, and by lines 54a, 54b, which are generally indicative of light beam boundaries. In other arrangements, the emitted light 54, 54a, 54b could have a spatially attenuated pattern to prevent CCD pixel saturation close to and outside of borders of tissue 64.

Other elements of FIG. 1B can be the same as or similar to elements of FIG. 1. For example, a mask 66 can be the same as or similar to the mask 26, an epi-illumination light source 56 can be the same as or similar to the epi-illumination light source 16, a camera 60 can be the same as or similar to the camera 20, a normalization processor 70 can be the same as or similar to the normalization processor 30, and a display 74 can be the same as or similar to the display 34.

For both the system 10 of FIG. 1 and the system 50 of FIG. 1B, methods of generating "normalized" images are described below using "un-normalized" images. Generation of a normalized fluorescence epi-illumination images involves collection of at least two separate images (i.e., two types of image data) that are combined to provide the normalized fluorescence epi-illumination image (or normalized image data). The two images include an image of the tissue (e.g., 24, FIG. 1) resulting from epi-illumination excitation light (e.g., 18, 18a, 18b, FIG. 1) generated by an epi-illumination light source (e.g., 16, FIG. 1), which is generally reflected from the tissue 24 (FIG. 1), and also an un-normalized image of emitted light from a fluorescent probe (i.e., a fluorochrome). The emitted light is excited by the excitation light 18, 18a, 18b. The image of the excitation light 18, 18a, 18b is also referred to herein as an intrinsic epi-illumination image and the image of the emitted light is also referred to herein as an un-normalized fluorescence epi-illumination image.

In some embodiments, two dark light images (i.e., background images that can contain, for example, stray light and noise) are also collected and used in combination with the above two images to generate the normalized fluorescence epi-illumination image. One dark light image can be generated using the same acquisition settings (gain, exposure time, etc.), which are used to capture the above-described intrinsic epi-illumination image, and the other dark light image can be generated using the same acquisition settings, which are used to capture the above-described un-normalized fluorescence epi-illumination image. Use of dark images will become apparent from equations below.

Similarly, generation of a normalized fluorescence transillumination image involves collection of at least two separate un-normalized images (i.e., two types of image data) that are combined to provide the normalized fluorescence transillumination image (or normalized image data). The two un-normalized images include an image of the tissue (e.g., tissue 24, FIG. 1) generated from transillumination excitation light (e.g., excitation light 14, FIG. 1) generated by a transillumination light source (e.g., source 12, FIG. 1), which passes through the tissue 24, and an image of emitted light from a fluorescent probe (i.e., a fluorochrome). The emitted light is excited by the excitation light 14. The image of the excitation 14 is also referred to herein as an intrinsic transillumination image and the image of the emitted light is also referred to herein as an un-normalized fluorescence transillumination image.

In some embodiments, two dark light images are also collected and used to generate the normalized fluorescence transillumination image. One dark light image can be generated using the same acquisition settings (gain, exposure time, etc.), which are used to capture the above-described intrinsic transillumination image, and the other dark light image can be generated using the same acquisition settings, which are used to capture the above-described un-normalized fluorescence transillumination image.

Similarly, for bioluminescence, at least two, but in some embodiments four, images can collected, i.e. the intrinsic image and dark image for excitation light (epi-illuminated or transilluminated) and the emitted image and dark image for bioluminescence.

For embodiments using dark images, the dark images need not be acquired in each measurement but can be acquired once and stored in memory. As described above, in some embodiments, the dark current images may not be used, especially if dark images have very low contrast. In some other embodiments, an equivalent subtraction method may be used.

For both normalized fluorescence epi-illumination imaging and normalized fluorescence transillumination imaging, the excitation light provided by the light source and the emitted light generated by the fluorescent probe can be at different wavelengths. The emitted light received to generate bioluminescence images and the excitation light employed in associated intrinsic light images can be at different wavelengths or at the same wavelength. In one particular embodiment, the emitted light is near infrared light and the excitation light is also near infrared light but at a shorter wavelength. In one particular embodiment of bioluminescence imaging, the emitted light contains visible and near-infrared spectral components and the excitation light contains similar spectral components.

The following equations can be used in a method to generate normalized and noise-reduced fluorescence epi-illumination images and normalized and noise-reduced transillumination fluorescence images. Such a method can be performed in a system similar to systems 10, 50 described above in conjunction with FIGS. 1 and 1B, respectively. It will be understood that, in some embodiments, the un-normalized images described below can be generated by the camera 20 of FIG. 1 or the camera 60 of FIG. 1B. The normalized images described below (and also the noise reduced un-normalized images), which can be generated by further processing and/or combination of the un-normalized images, can be generated by the normalization processor 30 of FIG. 1 or the normalization processor 70 of FIG. 1B.

An un-normalized and noise-reduced fluorescence epi-illumination image, Ie, can be expressed as:

$$I_e = I_{fe} - I_{fn} \qquad \text{(Eq. 1)}$$

where $I_{fe}$ is the fluorescence image generated when using an epi-illumination light source (e.g. light source 16, FIG. 1) and $I_{fn}$ is the background camera noise image (i.e., a dark image or a constant), respectively. $I_{fn}$ can be acquired with identical acquisition and experimental parameters as $I_{fe}$ but in the absence of excitation light, or it can be approximated by an equivalent constant value, which can be based on an experimental measurement. Hereafter, the image, $I_e$, is referred to as an un-normalized noise-reduced fluorescence epi-illumination image, or more simply an un-normalized fluorescence epi-illumination image, where the noise is presumed.

Similarly an un-normalized and noise-reduced fluorescence transillumination image, $I_t$, can be expressed as:

$$I_t = \sum_{k=1}^{Ns} g(k)(I_{ft}(k) - I_{fn})_{>Tf} \qquad \text{(Eq. 2)}$$

where Ns is the number of back-illuminating transillumination light sources (e.g., light sources 12, FIG. 1) where (Ns≥1), $I_{ft}(k)$ is a fluorescence transillumination image obtained by illuminating the $k^{th}$ transillumination light source, and $I_{fn}$ is a corresponding noise image (also including an offset) obtained under identical conditions but with no illumination by an excitation light source (i.e., a dark image). The factor g(k) is a percentage coefficient that is included to correct for the variation of individual transillumination light source strengths compared to a median source strength as calculated based on the relative strength of each source, which values are measured, for example, through a homogenous intralipid. Tf is a threshold value.

All fluorescence image values above the threshold, Tf, are summed together (superimposed) to yield the un-normalized noise-reduced fluorescence transillumination image. In one particular embodiment, the threshold, Tf, is set at 10 times the standard deviation of the photon counts seen in the $I_{fn}$ image. The value of the threshold, Tf, is selected to prevent noise, or to prevent image signals having a low signal to noise ratio from being included in the un-normalized fluorescence transillumination image, $I_t$. Hereafter, the image, $I_t$, is referred to as an un-normalized noise-reduced fluorescence transillumination image, or more simply an un-normalized fluorescence transillumination image, where the noise subtraction may be presumed.

The above un-normalized fluorescence epi-illumination image, Ie, and the un-normalized fluorescence transillumination image, $I_t$, can be normalized in the following way. The normalization process divides the un-normalized images by corresponding intrinsic images (i.e. by an image of epi-illumination excitation light for epi-illumination imaging or by an image of transillumination excitation light for transillumination imaging).

A normalized fluorescence epi-illumination image, $U_e$, can be computed as:

$$U_e = \frac{a \cdot (I_{fe} - I_{fn})_{>Tf} + c_f}{b \cdot (I_{ee} - I_{en})_{>Te} + c_e} \qquad (Eq. 3)$$

where $I_{ee}$ is a epi-illumination image obtained at the excitation light wavelength (i.e., an intrinsic epi-illumination image, which is an image of the tissue generated from excitation light generated by a epi-illumination light source having reflected from the tissue) and $I_{en}$ is camera noise and offset obtained with no excitation from the light source (or dark image).

Normalized image performance depends upon the threshold values Tf (for the fluorescence epi-illumination image) and Te (for the intrinsic epi-illumination image). In one particular embodiment, Ue is set to zero unless the $I_{ee}$–$I_{en}$ denominator values are above the threshold, Te, and the $I_{fe}$–$I_{fn}$ values are above the threshold, Tf. Selection of the thresholds can be based upon noise statistics or empirical data. The selection can be made statically by selecting values a predetermined number of noise standard deviations of the noise image (for example, 20 standard deviations of the noise image, $I_{en}$), or adaptively. The constants $c_f$ and $c_e$ can also be statically or adaptively selected, and their purpose is to stabilize the image. The constants $c_f$ and $c_e$ can have a value of zero, depending on user preferences, or they may be small values to provide small offset values to stabilize the ratio and yield a more accurate visual result. In one particular embodiment, a default setting of cf=0 and $c_e$=1 is used to avoid division by zero. Similarly, factors a and b can implement a-priori information on the relative strength of fluorescence and excitation images, for example, the relative attenuation of the filters used in fluorescence measurements, compared to the filters used in excitation light measurements (see FIG. 2 below). In another arrangement, a=1 and b=1. However, depending upon the application, a and b can be other values given by pre-determined equations (for example functions of wavelength) or they can be experimentally measured.

Similarly a corresponding normalized fluorescence transillumination image, $U_t$, can be computed as:

$$U_t = \frac{a \cdot \sum_{k=1}^{Ns} g(k)(I_{ft}(k) - I_{fn})_{>Tf} + c_f}{b \cdot \sum_{k=1}^{Ns} g(k)(I_{et}(k) - I_{en})_{>Te} + c_e} \qquad (Eq. 4)$$

where $I_{et}$ is a transillumination image obtained at the excitation wavelength (i.e., an intrinsic transillumination image, which is an image of the tissue generated from excitation light generated by a transillumination light source having passed through the tissue) and $I_{en}$ is camera noise (dark image) obtained with no excitation from the excitation light source. Fluorescence and excitation transillumination images for each of the $N_s$ sources employed are summed (superimposed) after subtraction with the noise images $I_{fn}$ and $I_{en}$ and application of the $T_f$ and $T_e$ thresholds, respectively.

While noises $I_{fn}$ and $I_{en}$ are subtracted in the above equations 3 and 4, it should be understood that the similar normalization techniques apply to a system in which one or both of the noises are not subtracted.

It should be noted that, for the system 50 described in conjunction with FIG. 1B, which has only the one transillumination light source 52, a single transillumination image is obtained. In this case Eq. 2 and Eq. 4 are written without the summation terms.

An un-normalized fluorescence transillumination image (one transillumination light source) can be expressed as:

$$I_t = (I_{ft} - I_{fn})_{>Tf} \qquad (Eq. 5)$$

A normalized fluorescence transillumination image (one transillumination light source) can be expressed as:

$$U_t = \frac{a \cdot (I_{ft} - I_{fn})_{>Tf} + c_f}{b \cdot (I_{et} - I_{en})_{>Te} + c_e}, \qquad (Eq. 6)$$

where $I_{ft}$ and $I_{et}$ are now single transillumination images.

The intrinsic image can be an image that is obtained at a broader wavelength, i.e. at wavelengths that not only include the wavelength of the excitation light (e.g., 14, 18 of FIG. 1) but also the wavelength of resulting fluorescent light. Alternatively two "intrinsic" images can be obtained, one at the wavelength of the excitation light and one at the wavelength of the emitted (fluorescence) light, wherein a combination of the two can be used for normalization, for example, a linear combination or a weighted product.

In the above-described case of intrinsic image generation in which the intrinsic image is obtained at the broader wavelength range that includes the fluorescence wavelength, the fluorescence image can first be subtracted from the intrinsic image obtained, i.e. an image generated using an excitation light having a spectral response that is similar to the excitation and emission spectral responses, i.e. $I_{ee} = I_{ee}' - I_{fe}$ and $I_{et} = I_{et}' - I_{ft}$, where, as described above, $I_{ee}$ is an epi-illumination image obtained at the wavelength range of the extended excitation light source, $I_{et}$ is a transillumination image obtained at the wavelength range of the extended excitation light source, $I_{fe}$ is the fluorescence image generated when using an epi-illumination light source, and, $I_{ft}$ is the fluorescence image generated when using a transillumination light source. In this case, $I_{ee}'$ and $I_{et}'$ are intrinsic images over multiple wavelengths corresponding to the excitation and emission wavelengths obtained from epi-illumination and from transillumination, respectively, using excitation light having a wavelength at the excitation wavelength and also additional excitation light having a light spectrum that matches the wavelengths of emitted (fluorescence) light. The excitation light matching the fluorescence spectrum can be used to capture fluorescence propagation characteristics. This approach becomes particularly important for cases where the excitation light is in the visible wavelength range and the fluorescent light is in the near-infrared wavelength range. While the above is described generically, significant accuracy can be achieved by appropriately selecting the range and response over which the $I_{ee}'$ and $I_{et}'$ are obtained.

For bioluminescence imaging, Eq. 1, Eq. 3, and Eq. 5 (un-normalized epi-illumination, normalized epi-illumination, and un-normalized fluorescence transillumination images, respectively) can remain substantially unchanged, but $I_{fx}$ is interpreted to be associated with bioluminescence rather than with fluorescence. In normalized bioluminescence imaging, images can be normalized with intrinsic images obtained at a selected propagation wavelength range that best matches the wavelength of the bioluminescence systems. Therefore, excitation light can also include light having a spectrum that matches the wavelengths of the bioluminescence. Eq. 3 provides a normalized bioluminescence epi-illumination image.

For bioluminescence imaging, Eq. 2, used for multiple un-normalized fluorescence transillumination images, is not used. Also, for normalized transillumination bioluminescence imaging, Eq. 4, which applies to multiple transillumination light sources, can be instead expressed as:

$$U_t = \frac{a \cdot (I_{ft} - I_{fn})_{>Tf} + c_f}{b \cdot \sum_{k=1}^{Ns} g(k)(I_{et}(k) - I_{en})_{>Te} + c_e} \quad \text{(Eq. 7)}$$

and Eq. 6 for normalized bioluminescence transillumination imaging using one transillumination light source becomes:

$$U_t = \frac{a \cdot (I_{ft} - I_{fn})_{>Tf} + c_f}{b \cdot (I_{et} - I_{en})_{>Te} + c_e}. \quad \text{(Eq. 8)}$$

The modification in Eq. 7 (compared with Eq. 4) shows a non-dependence of the bioluminescence signal on the excitation light sources, therefore, the summation as a function of light sources is dropped. Similarly it should be pointed out that Eq. 7 and Eq. 8 are more generic in nature as they do not explicitly direct the geometry by which bioluminescence images are captured. However they assume that excitation light propagates from similar tissues as from which the bioluminescence signal is collected. One embodiment for normalized imaging given by Eq. 3 applied to bioluminescence of superficial structures, wherein bioluminescence images are corrected for tissue attenuation in epi-illumination mode.

Figure 9A:
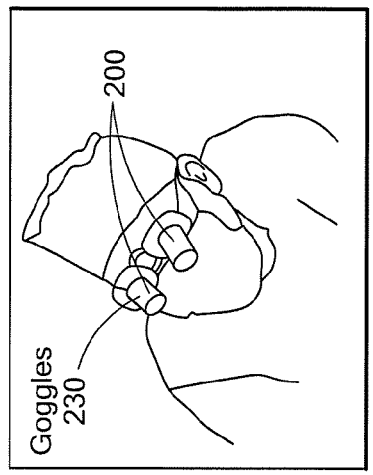
FIG. 9A is a pictorial of another system used for intra-operative imaging, including goggles that can be worn by a surgeon.
Figure 9:
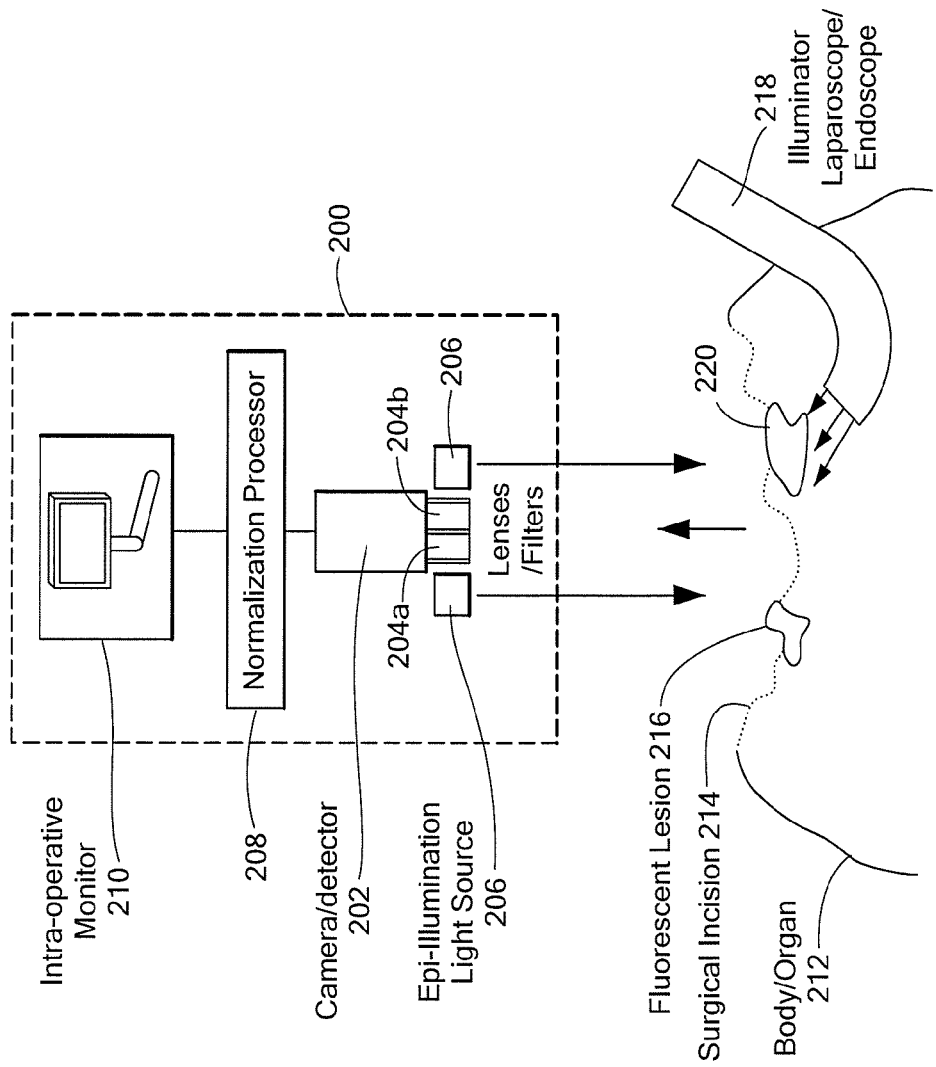
FIG. 9 is a pictorial of a system used for intra-operative imaging, including a portable camera/illuminator combination, a normalization processor, and a monitor, and, in some embodiments, a flexible probe (illuminator/laparoscope/endoscope)
Figure 10:
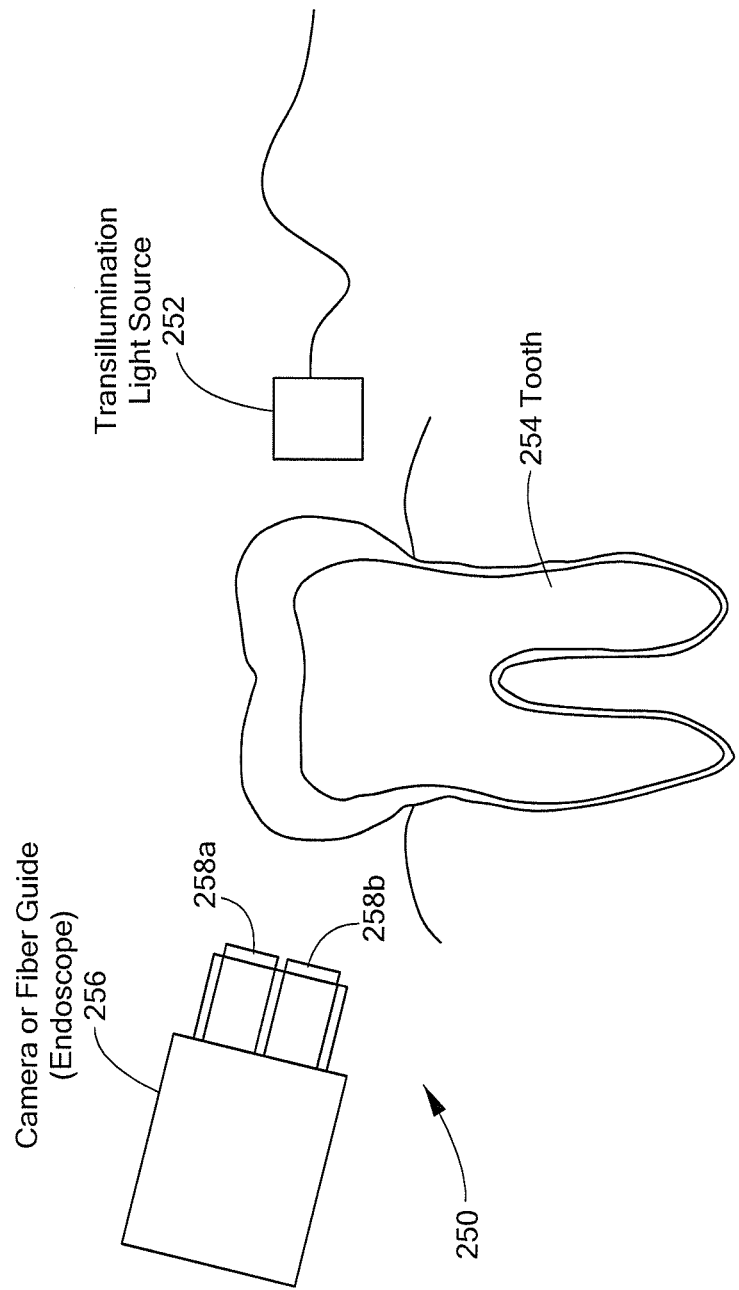
FIG. 10 is a pictorial of a system that can be used for dental imaging.

It should be appreciated that the normalization methods described above are generic in nature and can be applied in both systems 10, 50 of FIG. 1 and FIG. 1B (and also systems shown in FIGS. 9, 9A, and 10).

An alternative normalization approach referred to herein as a "per-source" normalization approach, which independently normalizes each source that is time, frequency, or wavelength encoded and then adds the normalized results together. This normalization can be implemented with any light source geometry, even if the light sources are placed on the sides or the top-side of the tissue being imaged.

In accordance with Eq. 4 and the above description, a per-source normalization image can be expressed as:

$$U_{psn} = \sum_{k=1}^{Ns} \frac{a \cdot (I_{ft}(k) - I_{fn})_{>Tf} + c_f}{b \cdot (I_{et}(k) - I_{en})_{>Te} + c_e} \quad \text{(Eq. 9)}$$

The thresholds $T_f$ and $T_e$ can be constant for all values k or can be $T_f = T_f(k)$ and $T_e = T_e(k)$, which indicates that each ratio, applied for each individual light source, is threshold differently. In one embodiment, $T_e$ is an adaptive threshold that is scaled as a function of $I_{et}(k)$ intensity, for example $T_e = 0.1 * I_{et}(k)$ and $T_f$ is a constant, for example, 5 times the standard deviation of noise. Image pixels that give denominator values that are less than $T_e$ are not calculated into the summation.

For all equations 1-9, a normalized image may be further processed for display by logarithmically or exponentially relating a final normalized image to the above-calculated normalized image. A normalized image for display is selected depending on the dynamic range of the values in the above-calculated normalized image.

Subtraction of images in equations above can comprise subtracting pixel magnitudes of a dark image (noise image) from co-registered pixels of an un-normalized emitted light image (fluorescence or bioluminescence, epi-illumination or transillumination). Division of images in equations above can comprise dividing pixel magnitudes of an un-normalized emitted light image (fluorescence or bioluminescence, epi-illumination or transillumination) by magnitudes of co-registered pixels of an intrinsic excitation light image (epi-illumination or transillumination).

While it is described above that the epi-illumination light source 56 and the transillumination light source 52 are adapted to generate excitation light, in other arrangements, the epi-illumination light source 56 and/or the transillumination light source 52 are adapted to generate incident light having the wavelength of the excitation light and also other wavelengths. The same is true for other arrangements, for example, arrangements shown in FIGS. 9, 10, and 11, which are described more fully below.

Figure 1C:
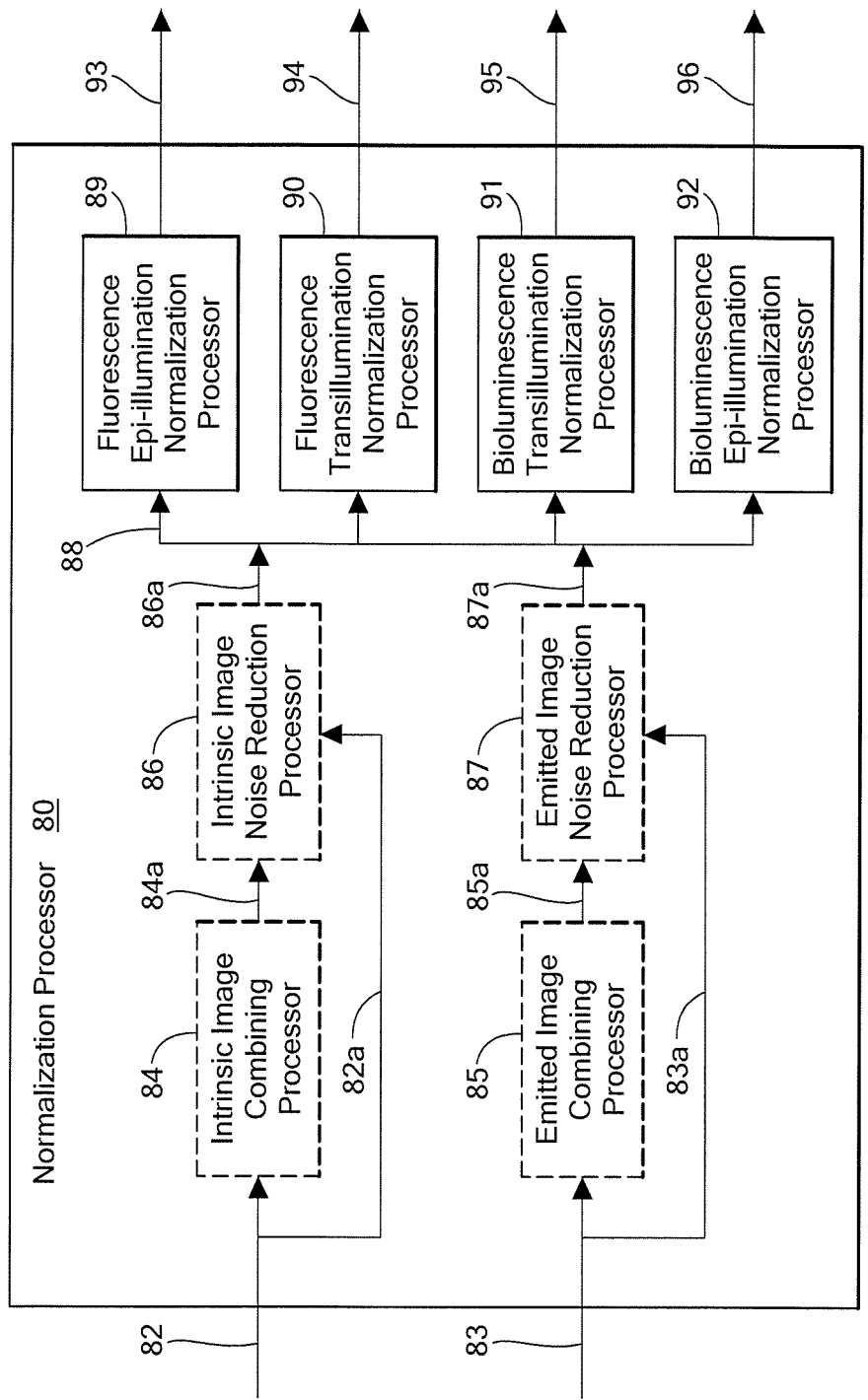
FIG. 1C is a block diagram showing further details of the normalization processors of FIGS. 1 and 1B.

Referring now to FIG. 1C, a normalization processor 80, which may be the same as or similar to the normalization processors 30, 70 of FIGS. 1 and 1B, respectively, receives one or more intrinsic excitation light images on path 82 and one or more un-normalized emitted light images on path 83 and generates one or more of a variety of types of a normalized light images made available on signal paths 93-96.

The intrinsic excitation light images on path 82 are received by an optional intrinsic image combining processor 84. The intrinsic image combining processor 84 can be adapted to combine (e.g. superimpose) intrinsic transillumination images for systems having a plurality of transillumination light sources, e.g., the system 10 of FIG. 1, and to generate a single intrinsic image at an output thereof on path 84a. In other arrangements, the intrinsic image combining processor 84 is adapted to combine intrinsic images generated at a plurality of wavelengths. For a system having only one transillumination light source, for example, the system 50 of FIG. 1B, or a system for which the excitation light source generates light at only the excitation light wavelength, the intrinsic image combining processor 84 is not needed.

Similarly, the un-normalized emitted light images on path 83 are received by an optional emitted image combining processor 85. The emitted image combining processor 85 is adapted to combine (e.g. superimpose) emitted transillumination images for systems having a plurality of transillumination light sources, e.g., the system 10 of FIG. 1, and to generate a single un-normalized emitted light image at an output thereof on path 85a. For a system having only one transillumination light source, for example, the system 50 of FIG. 1B, the emitted image combining processor 85 is not needed.

An intrinsic image noise reduction processor 86 is adapted to receive the single intrinsic image on path 84a and also a dark image on path 82a (background image). The intrinsic image noise reduction processor 86 is further adapted to combine the single intrinsic image and the dark image to provide a noise-reduced intrinsic image on path 86*a*. In some embodiments in which noise reduction is not performed, the intrinsic image noise reduction processor 86 is not used and the single intrinsic image on path 84*a* is used in place of the noise-reduced intrinsic image on path 86*a*.

Similarly, an emitted image noise reduction processor 87 is adapted to receive the single un-normalized emitted light image on path 85*a* and also a dark image on path 83*a* (background image). The emitted image noise reduction processor 87 is further adapted to combine the single un-normalized emitted light image on path 85*a* and the dark image on path 83*a* to provide a noise-reduced un-normalized emitted light image on path 87*a*. In some embodiments in which noise reduction is not performed, the emitted image noise reduction processor 87 is not used and the un-normalized emitted light image on path 85*a* is used in place of the noise-reduced un-normalized emitted light image on path 87*a*.

When the noise-reduced intrinsic image on path 86*a* is a noise-reduced intrinsic epi-illumination image and when the noise-reduced un-normalized emitted light image on path 87*a* is a noise-reduced un-normalized fluorescence epi-illumination image, those images are provided to a fluorescence epi-illumination normalization processor 89 adapted to generate a normalized fluorescence epi-illumination image on path 93.

When the noise-reduced intrinsic image on path 86*a* is a noise-reduced intrinsic transillumination image and when the noise-reduced un-normalized emitted light image on path 87*a* is a noise-reduced un-normalized fluorescence transillumination image, those images are provided to a fluorescence transillumination normalization processor 90 adapted to generate a normalized fluorescence transillumination image on path 94.

When the noise-reduced intrinsic image on path 86*a* is a noise-reduced intrinsic transillumination image and when the noise-reduced un-normalized emitted light image on path 87*a* is a noise-reduced un-normalized bioluminescence transillumination image, those images are provided to a bioluminescence transillumination normalization processor 91 adapted to generate a normalized bioluminescence transillumination image on path 95.

When the noise-reduced intrinsic image on path 86*a* is a noise-reduced intrinsic epi-illumination image and when the noise-reduced un-normalized emitted light image on path 87*a* is a noise-reduced un-normalized bioluminescence epi-illumination image, those images are provided to a bioluminescence epi-illumination normalization processor 92 adapted to generate a normalized bioluminescence epi-illumination image on path 96.

The normalization processor 80 is adapted to generate the four types of images on paths 93-96, wherein each one of the images can be noise reduced or not. Furthermore, the normalized fluorescence transillumination image provided on path 94 and the normalized bioluminescence transillumination image provided on path 95 can be generated using one excitation transillumination light source or a plurality of excitation transillumination light sources (superimposed via the processors 84, 85). However, in other arrangements, only one or more of the processors 89-92 are included in the normalization processor 80.

Referring now to FIG. 2, a camera 100, which can be the same as or similar to the camera 20 of FIG. 1 and the camera 60 of FIG. 1B, is adapted to receive and process light.

The light received by the camera 100 can include intrinsic excitation light resulting from excitation light generated by an epi-illumination light source, and/or fluorescent light emitted by a tissue in response to the excitation light generated by the epi-illumination light source. The light received by the camera 100 can also include excitation light resulting from excitation light generated by a transillumination light source, and/or fluorescent light emitted by a tissue in response to the transillumination light generated by the transillumination light source. The light received by the camera 100 can also include bioluminescence light naturally generated within the tissue.

The camera 100 can include an intrinsic image processor 102, which is adapted to receive the above-described excitation light resulting from either the epi-illumination light source or the transillumination light source that has impinged upon and interacted with the tissue, and which is also adapted to generate an intrinsic image (i.e., intrinsic image data). The camera 100 can also include a fluorescence image processor 104, which is adapted to receive the above-described fluorescent light resulting from either the epi-illumination light source or the transillumination light source that has been emitted from the tissue, and which is also adapted to generate an un-normalized fluorescence image (i.e., un-normalized fluorescence images data). The intrinsic image processor 102 and the fluorescence image processor 104 can be provided, for example, by way of or in conjunction with an optical filter (excitation light filter 106) adapted to pass the excitation light and another optical filer (fluorescent light filter 108) adapted to pass the fluorescent light. The intrinsic image processor 104 and the fluorescence image processor 106 can operate at substantially the same time or in sequence to provide the intrinsic image (i.e., intrinsic image data) and the un-normalized fluorescence image (i.e., un-normalized fluorescence image data). Since the excitation light received by the camera 100 may be at a greater intensity than the fluorescent light, in some embodiments, the excitation light filter 106 can include a light attenuating filter, for example, a neutral density filter.

In some embodiments, polarizers (not shown) can be further used to preferentially select polarization modes. The polarizers can be used at the epi-illumination light source (e.g. 56, FIG. 1B), at the transillumination light source (e.g., 52, FIG. 1B), at the intrinsic portion 102 of the camera 100, and/or at the fluorescence processor 104 of the camera 100. The polarizers can facilitate more superficial imaging (when the same orientation polarization filters are used at each end of a light path) or deeper imaging (when cross-polarizers are used). In addition, polarizers can be used to better separate emission (fluorescence or bioluminescence) from excitation light by polarizing the emission light with one polarization direction and detecting emitted light in with a cross polarization.

While the fluorescence image processor 104 is described above, it should be understood that the same processor can be used to receive light resulting from bioluminescence and to form a bioluminescence image. While the excitation light filter 106 is described above, in other arrangements, the excitation light filter 106 is replaced with an incident light filter adapted to pass a plurality of wavelengths.

Referring now to FIG. 2A, another camera 150, which can be the same as or similar to the camera 20 of FIG. 1 and the camera 60 of FIG. 1B, is adapted to receive and process light. The camera 150 can include a filter wheel assembly 152 adapted to rotate and to select either an excitation light filter 154 or a fluorescent light filter 154. An image processor 158 is adapted to generate an intrinsic image or an un-normalized fluorescence image accordingly.

Unlike the camera 100 of FIG. 2, the camera 150 has only one image processor 158, which is used to sequentially provide both the intrinsic image (i.e., intrinsic image data) and the un-normalized fluorescence image (i.e. un-normalized fluorescence image data). Since the excitation light received by the camera 100 may be at a greater intensity than the fluorescent light, in some embodiments, the excitation light filter 154 can include a light attenuating filter, for example, a neutral density filter. While the excitation light filter 154 is described above, in other arrangements, the excitation light filter 154 is replaced with an incident light filter adapted to pass a plurality of wavelengths.

Before describing a series of images presented below, phantoms used to generate the images are described. A first phantom (used in images of FIGS. 3, 3A, and 4) was relatively spatially-homogenous and included two diffusive and fluorescent tubes placed 5 mm apart, which were immersed in a chamber. The tubes were glass capillaries ~1.5 mm diameter sealed on one end, containing 1% intralipid solution, 25 ppm of India ink, and 200 nm of Cy 5.5 dye to simulate varying absorption and fluorescence emanating from a superficial tumor. The chamber was further filled with the same solution of intralipid and ink but without the fluorochrome. The first phantom was placed at various depths in the chamber and was used to assess the relative performance of the above described normalization method as a function of phantom depth.

Figure 5:
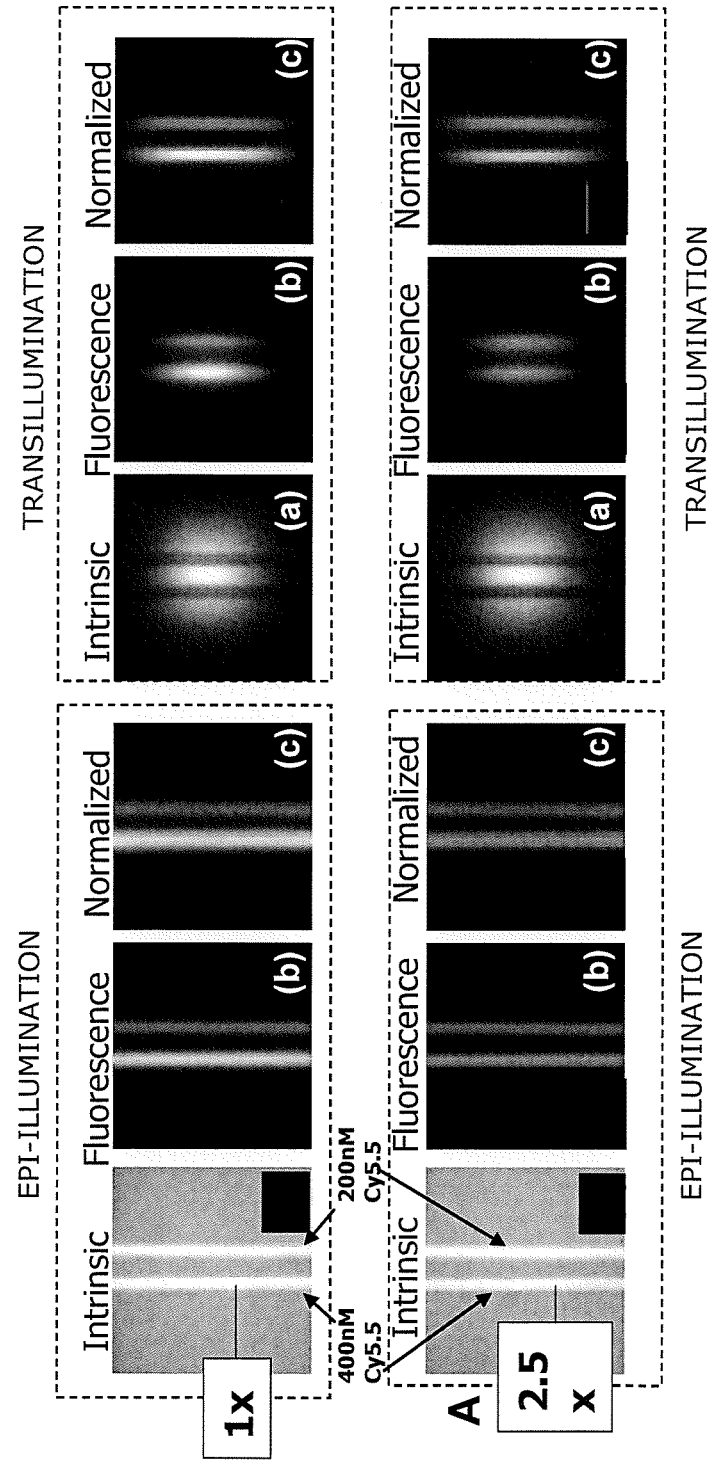
FIG. 5 is a series of images of a phantom showing an intrinsic epi-illumination image at the excitation light wavelength, a fluorescence epi-illumination image, and a normalized fluorescence epi-illumination image.

A second phantom (used in images of FIGS. 5-5C) employed the same relative homogenous background and a two-tube arrangement as the first phantom but employed two 3 mm diameter plastic tubes. The second phantom was used to examine accuracy of the two normalization methods as a function of varying optical properties. In these experiments the left tube was filled with 400 nm of Cy5.5 whereas the right tube contained 200 nm of Cy5.5. Both tubes and the background medium were filled with the same solution of 1% intralipid solution and 25 ppm of India ink (FIGS. 5 and 5B). Subsequently the absorption of the left tube was increased to 2.5× the background absorption concentration (FIGS. 5A and 5C). The second phantom was used to examine robustness of the normalized imaging methods with respect to varying background optical properties.

A third phantom was used in a first animal experiment (shown in FIGS. 6 and 6A) to generate images of a nude mouse post-mortem. This experiment demonstrated the merits of normalized transillumination in resolving deep-seated activity, better than epi-illumination. It also demonstrated how normalized epi-illumination can result in reducing false positives. The third phantom included a 1.8 mm diameter glass tube filled with intralipid and 400 nm of Cy5.5 dye, which was inserted in the animal through the esophagus until it reached the middle of the torso of the animal. Then the animal was placed in the imaging chamber and all image sets described by Eqs. 1-4 were obtained.

Figure 6:
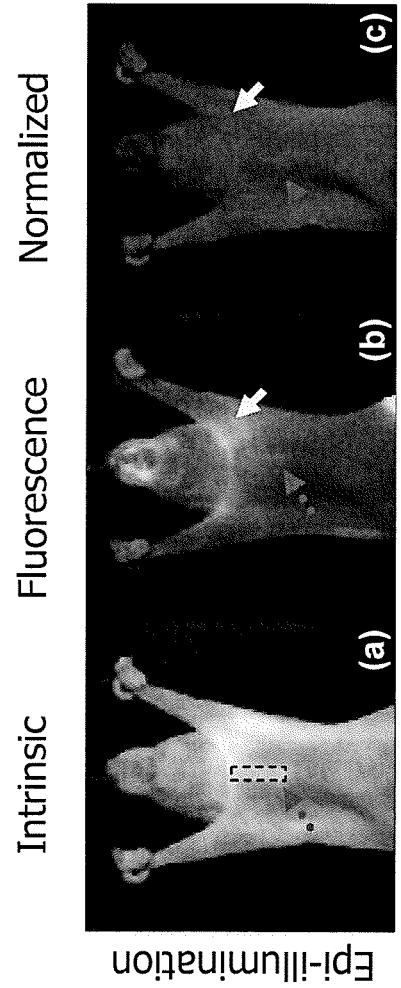
FIG. 6 is a series of images of a mouse showing an intrinsic epi-illumination image at the excitation light wavelength, a fluorescence epi-illumination image, and a normalized fluorescence epi-illumination image.
Figure 6A:
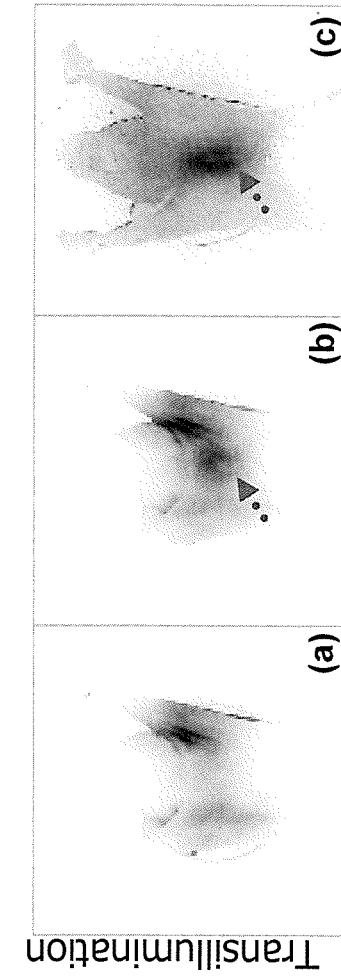
FIG. 6A is a series of images of the mouse of FIG. 6 showing an intrinsic transillumination image at the excitation light wavelength, a fluorescence transillumination, and a normalized fluorescence transillumination image.
Figures 7, 7A:
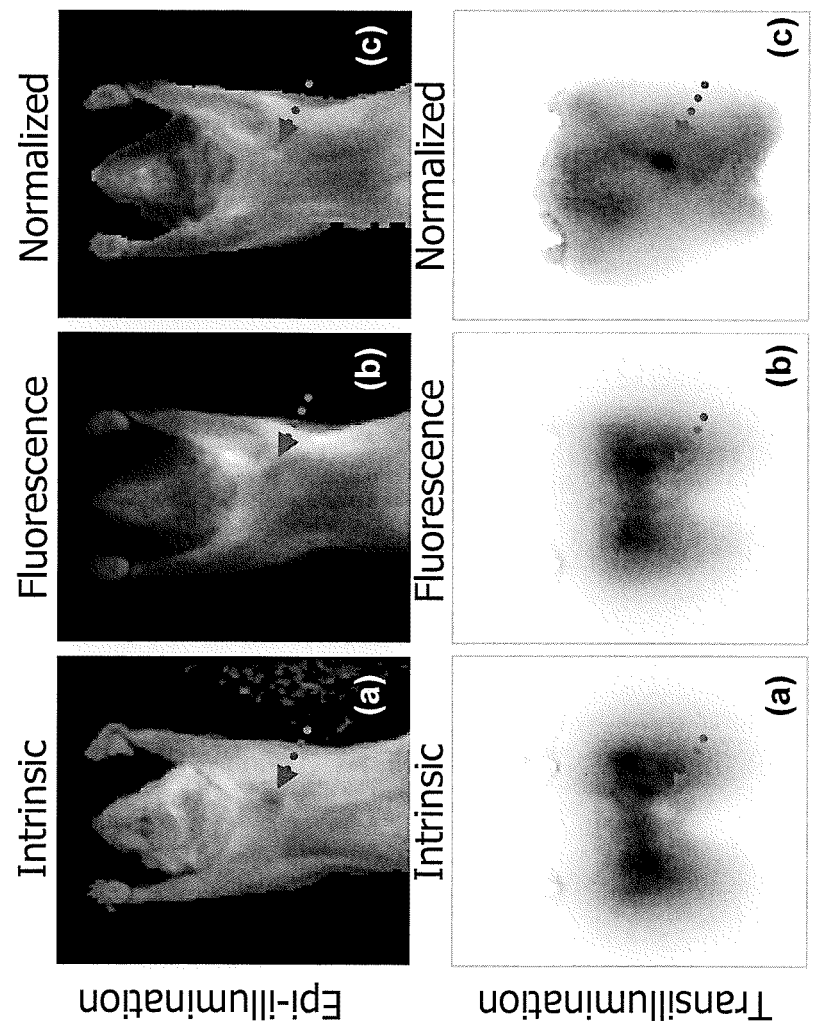
FIG. 7 is a series of images of another mouse showing an intrinsic epi-illumination image at the excitation light wavelength, a fluorescence epi-illumination image, and a normalized fluorescence epi-illumination image.
FIG. 7A is a series of images of the mouse of FIG. 7 showing an intrinsic transillumination image at the excitation light wavelength, a fluorescence transillumination image, and a normalized fluorescence transillumination image.

Images shown in FIG. 6A and FIG. 7A are negative images. However, positive images could equally well be generated and shown. It will also be understood that the intrinsic, un-normalized epi-illumination fluorescence, un-normalized transillumination fluorescence, normalized epi-illumination fluorescence, and normalized transillumination fluorescence images presented in FIGS. 6, 6A, 7, and 7A are all processed to remove background noise, for example, as in equations 1-4 above.

Referring now to FIG. 3, normalized fluorescence epi-illumination images of the first phantom are shown in panels (a)-(e), where the above-described tubes are placed at different depths in the chamber as indicated at 0, 1, 3, 5 and 7 mm away from a front glass window of the chamber. At a depth of 0 mm the tubes are physically in contact with the front window. The images in panels (a)-(e) are scaled to their maximum, since signal intensity drops exponentially with depth.

In this particular experiment, fluorescence epi-illumination imaging quality appears reduced as a function of depth. The tubes of the first phantom are practically not detectable at a depth of 7 mm. However, normalized fluorescence epi-illumination imaging yields significant resolution of the tubes at 0 mm. The two tubes are clearly resolved at 0 mm (when they are in contact with the front window). In contrast, it will be shown below, that at 0 mm, the tubes are less well resolved in normalized fluorescence transillumination imaging.

Referring now to FIG. 3A, normalized fluorescence transillumination images of the first phantom are shown in panels (a)-(e). Again, the images in panels (a)-(e) are scaled to their maximum since signal intensity drops exponentially with depth.

The tubes are detected in all normalized transillumination images at a variety of depths, although resolution appears to deteriorate as a function of depth. Broadening of the detected image of the tubes is seen in the fluorescence transillumination images as a function of depth as expected. Moreover, as the arrows indicate, there is a length dependent broadening as well. However the ability of normalized transillumination to detect the tubes deeper than normalized epi-illumination (FIG. 3) is apparent and may be important for improving planar images of sub-surface activity and deep-seated activity.

Figure 4:
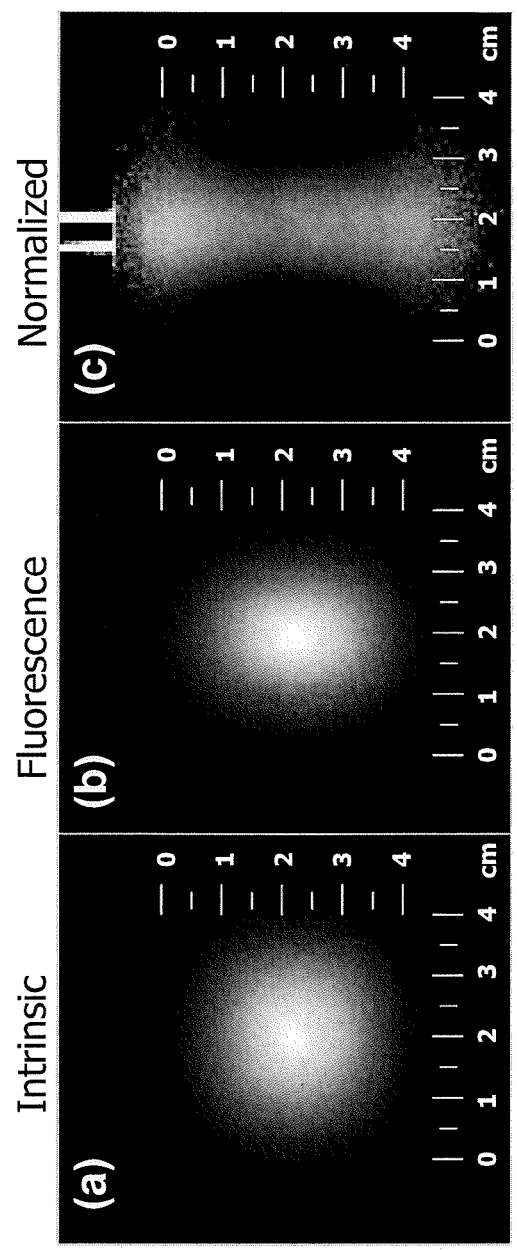
FIG. 4 is a series of images of the phantom, also seen in FIGS. 3 and 3A, showing an intrinsic transillumination image at an excitation light wavelength, a fluorescence transillumination image, and a normalized fluorescence transillumination image.

Referring now to FIG. 4, transillumination images of the first phantom are shown for the tubes placed at a depth of 5 mm. In panel (a), an intrinsic image of excitation light is generated. As described above, the excitation light corresponds to light from a transillumination light source having passed through tissue, here through the chamber and first phantom. The region of excitation light measures ~3×2 cm and its intensity exponentially drops outside this area.

In panel (b), an un-normalized fluorescence transillumination image is collected. As described above, the fluorescent light is emitted by a fluorescent probe within the tubes in response to the emitted light from the transillumination light source. The image of panel (b) is an un-normalized image, $I_t$, according to equation 2.

In panel (c), a normalized fluorescence transillumination image, $U_t$, is shown according to equation 4. The image, $U_t$, more accurately represents a true length of the tubes than the image, It, of panel (b). This is because the tubes are not covered homogeneously by the excitation light of panel (a). It would be advantageous to homogeneously illuminate the complete region of interest, however, as shown, the normalization can accurately represent dimensions of the tubes even when inhomogeneous excitation light is used. However, due to an asymmetry of the excitation light field of panel (a), there is an asymmetry of resolved "shape" at the ends of the image of the tubes (panel (c)).

Normalized fluorescence transillumination imaging is seen to be less sensitive to illumination field variations and also less sensitive to depth than normalized fluorescence epi-illumination imaging and than un-normalized fluorescence transillumination imaging. However, as shown by comparing FIG. 3, panel (a), with FIG. 3A, panel (a), normalized fluorescence epi-illumination imaging can be seen to provide higher resolution images than normalized fluorescence transillumination imaging for objects near a surface of a diffuse medium. This advantage is reduced even at a fluorescent probe depth of 1 mm below the surface.

Further experimental results described below show both normalized fluorescence transillumination images and normalized fluorescence epi-illumination images.

Referring now to FIGS. 5-5C, images were obtained with fluorescence epi-illumination and fluorescence transillumination imaging of the second phantom described above. As described above, the second phantom includes two tubes immersed in a solution of 1% intralipid solution and 25 ppm of India ink. In FIGS. 5 and 5B the tubes contained 25 ppm of India ink, i.e. the same as the background concentration. In FIGS. 5A and 5C the left tube contained 60 ppm India ink, i.e. ~2.5× the background ink concentration.

Referring first to FIGS. 5 and 5A, panels show intrinsic (excitation) light images (panels (a)), un-normalized fluorescence epi-illumination images (panels (b)), and normalized fluorescence epi-illumination images (panels (c)), respectively. By comparing the un-normalized fluorescence epi-illumination images (panels (b)) with the normalized fluorescence epi-illumination images (panels (c)), the effect of added absorption of the left tube can be seen. At 2.5× concentration (FIG. 5A) the un-normalized fluorescence image (panel b)) show only a 1.26:1 intensity ratio over the right tube where the actual ratio is 2:1 as shown at 1× concentration (panel b, FIG. 5). However, the normalized fluorescence images (panels (c)) show an improved ratio of 1.41:1.

Referring now to FIGS. 5B and 5C, images are of the same phantom as in FIGS. 5 and 5A including the above-described 1× or 2.5× ink concentration contained in the left tube as indicated. Panels show transillumination intrinsic images (panels (a)), un-normalized fluorescence transillumination images (panels (b)), and normalized fluorescence transillumination images (panels (c)), respectively.

Here, the un-normalized fluorescence transillumination images (panels (b)) show a 1.11:1 ratio, which is worse than the epi-illumination un-normalized fluorescence images (panels (b)) of FIGS. 5 and 5A. However, the normalized fluorescence transillumination images (panels (c)) show a ratio of 1.58:1, which is the better than the normalized fluorescence epi-illumination images (panels (c)) of FIGS. 5 and 5A. Therefore, normalized fluorescence transillumination imaging is shown to accurately measure fluorescence activity, here of superficial volumes, when the background optical properties are heterogeneous, as is the case when imaging most tumors and other diseases and medical conditions.

Referring now to FIG. 6, panels (a)-(c) show an epi-illumination intrinsic image, an un-normalized fluorescence epi-illumination image, and a normalized fluorescence epi-illumination image, respectively, of a nude mouse implanted with a fluorescent tube post-mortem. Panel (a) also shows an approximate position of the tube (see dark arrows) in the viewing plane as indicated by a dashed outline (repeated in panels (b) and (c)), found by measuring the insertion distance and by post-experiment surgical removal. The normalized fluorescence epi-illumination image of panel (c) does not show the implanted tube. In fact, the normalized image of panel (c) has less contrast than the un-normalized image of panel (b).

A white arrow in panel (b) shows fluorescence where no fluorescence signal should be present in the un-normalized fluorescence image. This region of fluorescence is reduced in the normalized image of panel (c), as is also shown by a white arrow in panel (c). This reduction shows that the normalization method can reduce false positives.

Skin auto-fluorescence and bleed through signals (e.g., reception of direct light along paths from the light source to the camera) appear in standard un-normalized fluorescence epi-illumination images, and normalization provides a more uniform epi-illumination image with fewer artifacts. Therefore, a very low or no signal image in fluorescence is expected, since there is very low auto-fluorescence in the near infrared. This is shown by the low contrast normalized image (panel (c)).

Another advantage of the normalized fluorescence epi-illumination image is that it can better identify an absence of fluorescence. This is an important feature for intra-operative imaging, laparoscopic imaging, endoscopy, and small animal imaging, since it accounts for variations and reflections of the excitation light that may bleed through to the camera or that may selectively excite more background auto-fluorescence. Therefore normalized fluorescent epi-illumination imaging can offer improved imaging accuracy and performance when used for its negative predictive capability.

Referring now to FIG. 6A, panels (a)-(c) show an intrinsic image, an un-normalized fluorescent transillumination image, and a normalized fluorescence transillumination image, respectively, of the animal of FIG. 6. The tube (at arrows) is detected and it is better resolved in the normalized fluorescence transillumination image than in the normalized fluorescence epi-illumination image (panel (c), FIG. 6). The tube size is overestimated in panel (c) but its two-dimensional location in the viewing plane is well resolved. Transillumination imaging has been performed with mice in the presence or absence of matching fluids with very similar results.

The images of FIGS. 6 and 6A show that normalized transillumination imaging, and similarly normalized epi-illumination imaging, can operate in the absence of matching fluids. However, proper care should be taken to selectively attenuate light at the borders of the tissue and outside the borders of the tissue to yield optical matching to the dynamic range of the measurements to the light detector used.

Referring now to FIG. 7, panels (a)-(c) show an intrinsic epi-illumination image, a un-normalized fluorescent epi-illumination image, and a normalized fluorescence epi-illumination image, respectively, of an animal bearing a surface tumor with an ellipsoid shape of 4 mm×3 mm long and short axis dimensions, respectively, as determined by caliper measurements. The tumor is an Erb2 positive spontaneous tumor in the left mammary fat pad (right side as shown on the image). The animal was injected with a cathepsin-sensitive fluorescent probe. The tumor is indicated by an arrow on the images. This tumor was highly vascular and highly absorbing and was therefore seen darker than surrounding tissue on the intrinsic epi-illumination image shown in panel (a). A corresponding un-normalized fluorescence epi-illumination image shown in panel (b) does not identify the tumor. The normalized fluorescence epi-illumination image shown in panel (c) provides an image that appears more flat (i.e., the same intensity throughout the animal) and the tumor is now identifiable. However the detection ability is reduced due to other fluorescence activity within the animal, i.e., outside of the tumor, resulting from fluorochrome outside of the tumor.

Referring now to FIG. 7A, panels (a)-(c) show an intrinsic transillumination image, an un-normalized fluorescence transillumination image, and a normalized fluorescence transillumination image, respectively, of the animal of FIG. 7. The normalized image of panel (c) shows a marked fluorescence increase associated with the tumor (arrow). The tumor is not visible in panel (b), the un-normalized fluorescence transillumination image.

The animal of FIGS. 7 and 7A was injected with a fluorescence probe, therefore, it is expected that there is a remnant background fluorescence signal in tissues apart from the tumor. This higher background image signal is evident in panel (c) (compare to panel (c) of FIGS. 6A and 6B). However the detection improvement gained by the normalized fluorescence transillumination method is still evident.

The above system and methods can also apply to bioluminescence imaging, wherein an un-normalized bioluminescence image is normalized with an intrinsic epi-illumination image to yield a normalized bioluminescence epi-illumination image. While tissue emission apart from a tumor is less of an issue for bioluminescence than for fluorescence (autofluorescence), the normalization can nevertheless correct for attenuation heterogeneity across the animal surface, which can result from blood concentration heterogeneity, especially if a light source with spectral characteristics to match those of the emitted bioluminescence is used. Similarly the bioluminescence image can be normalized with an intrinsic transillumination image, and this may achieve a better result that than normalizing with an intrinsic epi-illumination image, especially when the bioluminescence is emitted from lesions deeper in the animal.

Figure 8:
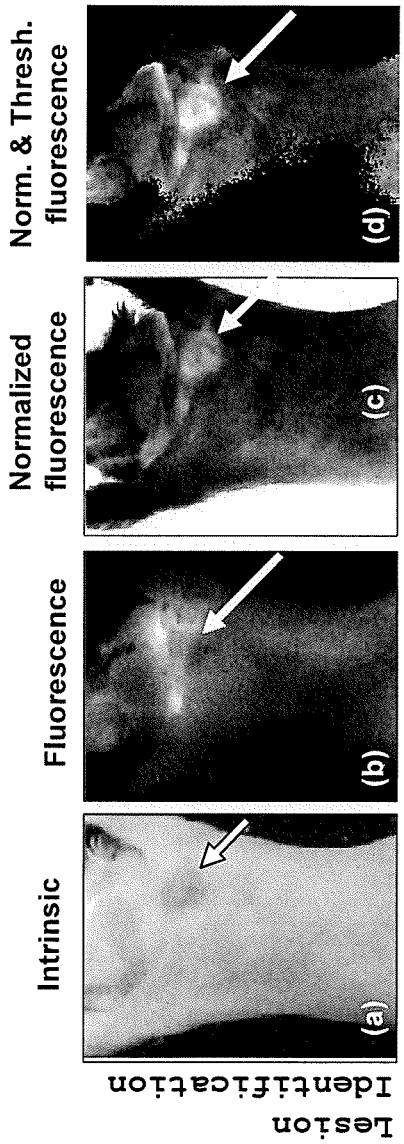
FIG. 8 is a series of images showing an intrinsic epi-illumination light image at the excitation wavelength, a fluorescence epi-illumination image, a normalized fluorescence epi-illumination image, and a normalized fluorescence epi-illumination image after the application of noise thresholds, showing detection of tumors.

Referring now to FIG. 8, images show another mouse having an Erb2 positive spontaneous tumor, which was imaged after the administration of a cathepsin sensitive activatable fluorescence probe. These images demonstrate improved images obtained with normalized epi-illumination imaging, which allow improved identification of the location of a fluorescent lesion (at arrows). It can be seen that normalized epi-illumination imaging can be useful for lesion identification when used in surgical operations, endoscopy, and laparoscopy. Here normalized images both before (panel (c)) and after (panel (d)) noise removal are shown.

Figure 8A:
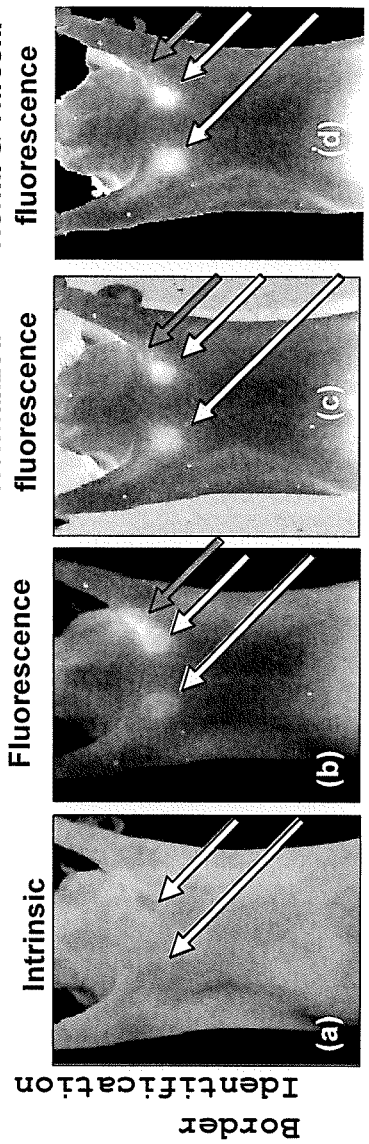
FIG. 8A is a series of images showing an intrinsic epi-illumination image at the excitation light wavelength, a fluorescence epi-illumination image, a normalized fluorescence epi-illumination image, and a normalized fluorescence epi-illumination image after the application of noise thresholds, showing detection of tumors.

Referring now to FIG. 8A, images show a mouse having two HT1080 tumors implanted in the left and right side of the mammary fat pads, which are imaged after the administration of a cathepsin sensitive activatable fluorescence probe. These images demonstrate improved images obtained with normalized epi-illumination imaging, which allow improved identification of tumor borders. It can be seen that normalized epi-illumination imaging can be useful for border identification when used in surgical operations, endoscopy, and laparoscopy. Images both before (panel (c)) and after (panel (d)) noise removal are shown.

FIGS. 8 and 8A show images related to techniques, which can be used in medical procedures, for example, intra-operative imaging, endoscopy, or laparoscopy used for the identification of lesions and their borders.

Referring again to FIG. 8, panels (a)-(d) show an epi-illumination intrinsic image, an un-normalized epi-illumination fluorescent light image, a normalized fluorescence epi-illumination image that assumes noise thresholds at zero, and a normalized fluorescence epi-illumination image that has been processed with noise threshold operations as described in Eq. 3, respectively. The images show an animal bearing a surface tumor, as indicated with an arrow, which appears dark on the intrinsic epi-illumination image (panel (a)). Due to tumor absorption of light, the tumor appears dark on the un-normalized fluorescence epi-illumination image (panel (b)). Some activity that can be observed at the top part of the tumor is not co-localized with the presence of the tumor, even if the animal has been injected with the same activatable fluorescent probe as in FIG. 7. Such activity at the borders of the tumor is typical in some un-normalized images and may be due to a local excitation field variation resulting from tissue heterogeneous absorption. Conversely the normalized fluorescence epi-illumination images of panels (c) and (d) correctly identify the location and size of the tumor. The image of panel (d) has been enhanced by the application of noise thresholds and by maximizing contrast. An additional smaller lesion also appears on the left side of the large tumor and this is visualized well in both normalized fluorescence images. However, in particular, the image of panel (d) demonstrates how the normalized fluorescence image can better show the total background fluorescence activity.

Referring again to FIG. 8A, images show the same configuration as shown in FIG. 8. A mouse has two HT1080 implanted tumors, which are indicated by arrows. Borders of the right tumor are not well differentiated since light "leaks" into the low absorbing skin fold that forms just above it. Therefore, the tumor appears as elongated. This characteristic may be drawback in surgical procedures where the exact tumor margins need to be identified so that unnecessary tissue damage during operation is minimized, especially, for example, in brain surgery. Conversely the normalized images of panels (c) and (d) better differentiate the tumor margins, which was also was correlated by actual tumor excision and invasive inspection.

Referring now to FIG. 9 a system 200 for intra-operative (i.e., imaging during an operation) procedures includes a camera 202, which can include two lenses and/or filters 204a, 204b. The camera 202 with filters 204a, 204b can be the same as or similar to the camera 100 (including filters 106, 108) of FIG. 2. The system 200 can also include an epi-illumination light source 206, which can, in one particular embodiment, be in the form of a ring illuminator. The camera can provide un-normalized images to a normalization processor 208, which can provide normalized images to a monitor 210.

It will be appreciated that the system 200 is similar to the system 10 of FIG. 1, however, the system 200 can be reduced in size so as to provide a system that can be more easily used during an operation.

In use, a body part or organ 212 can be exposed as shown, for example, by a surgical incision. A fluorochrome, which can be injected into the patient before or during the operation, and which tends to congregate at the site of a lesion 216, makes the lesion fluorescently reactive. As described above, the camera 202 can generate an intrinsic epi-illumination image and an un-normalized fluorescence epi-illumination image. The normalization processor 208 can generate a normalized epi-illumination fluorescence image and can send the normalized image to an intra-operative monitor 210, where it can be viewed by a surgeon.

In one particular embodiment, the intra-operative monitor 210 is in proximity to the operation theater so that the surgeon can see fluorescence indicative of disease on the monitor.

Also shown in FIG. 9, an illuminator/laparoscope/endoscope 218 (hereafter called a probe 218) can be used in a variety of ways. In one arrangement, the probe 218 provides a transillumination light source, which can be used so that the camera 202 can capture an intrinsic transillumination image and/or an un-normalized fluorescence transillumination image of a lesion 220. This probe can be used during surgery to complement the epi-illumination system 200 or it can provide only transillumination imaging without use of the epi-illumination light source.

In another arrangement, the probe 218 provides an epi-illumination light source, wherein the system 200 is coupled to a distal end of the probe 218 in order to generate both an intrinsic epi-illumination image and an un-normalized fluorescence epi-illumination image and also a normalized fluorescence epi-illumination image of the lesion 220 in response to the epi-illumination light source provided by the probe 218. Such arrangements will be better understood form the discussion below in conjunction with FIGS. 11 and 11A.

In some arrangements, the probe 218 can be manually manipulated during the operation to image selected structures or organs. Real-time normalization techniques, such as the one described by Eq. 4, can be implemented using fast image processing digital processors, and can provide accurate imaging independent of the exact pattern of the illumination field, which may vary when generating different illumination orientations when manipulating the probe 218.

The probe 218 can be placed, for example, on the side of or behind a lymph node to investigate or confirm the presence or absence of a fluorochrome indicative of a malignancy. The probe 218 can be placed behind an organ to identify fluorescence activity indicative of function or disease. This fluorescence is provided by a local or systemic administration of a fluorochrome.

In some embodiments, as described above, the probe 218 is an endoscope or laparoscope so that the fluorescence activity can be captured by the probe 218. These arrangements can be used, for example, in laparoscopy, minimally invasive surgery, endoscopy, and colonoscopy.

Referring now to FIG. 9A, in another embodiment, the system 200 of FIG. 9 is constructed entirely or in part within a miniaturized detection and visualization system, for example, goggles 230 or a transparent screen (not shown). These embodiments can allow, via the use of appropriate filters, co-registration of anatomical contrast, as would be naturally seen by the eye, in combination with fluorescence activity. For example, in one arrangement, the body/organ 212 is seen naturally and color contrast is added to indicate the presence of the fluorescence associated with a lesion.

In yet another embodiment, the system 200 is a portable system, for example a hand-held scanner.

Referring now to FIG. 10, a system 250 includes a transillumination light source 252 disposed on the opposite side of a tooth 254 from a camera 256. The camera 256 can have two filters 258*a*, 258*b*, and can be the same as or similar to the camera 100 of FIG. 2. The camera 256 can generate an intrinsic transillumination image and also and un-normalized fluorescence transillumination image of the tooth 254 and structures therein. In some arrangements the camera is instead an endoscope, which can be the same as or similar to the probe of FIG. 9. A normalization processor (not shown) and monitor (not shown) can be coupled to the camera 256 in order to generate normalized images.

In this embodiment, the transillumination light source 252 and the camera 256 are introduced in the mouth and disposed about the tooth 254 as shown. In some arrangements, the camera 256 also includes an epi-illumination light source (not shown), which can be the same as or similar to the epi-illumination light source 206 of FIG. 9.

The system 250 can generate normalized fluorescence transillumination images and/or normalized fluorescence epi-illumination images of dental fluorescence contrast. In some embodiments, the system 250 can use native tissue auto-fluorescence, which can be excited by the excitation light source 252. However, in other embodiments, extrinsically or topically administered external fluorochromes with molecular or functional specificity can be applied to the tooth 254.

The system 250 can also be used to investigate other oral cavity diseases, for example gum disease or oral cancers. The system 250 can be used in combination with other non-invasive imaging systems, for example X-ray systems, to provide further diagnostic capability.

Figure 11A:
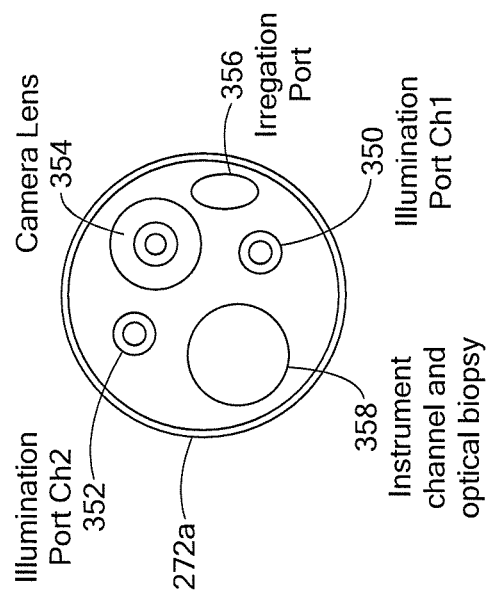
FIG. 11A is a pictorial showing greater detail of a face of the colposcopic probe of FIG. 11.
Figure 11:
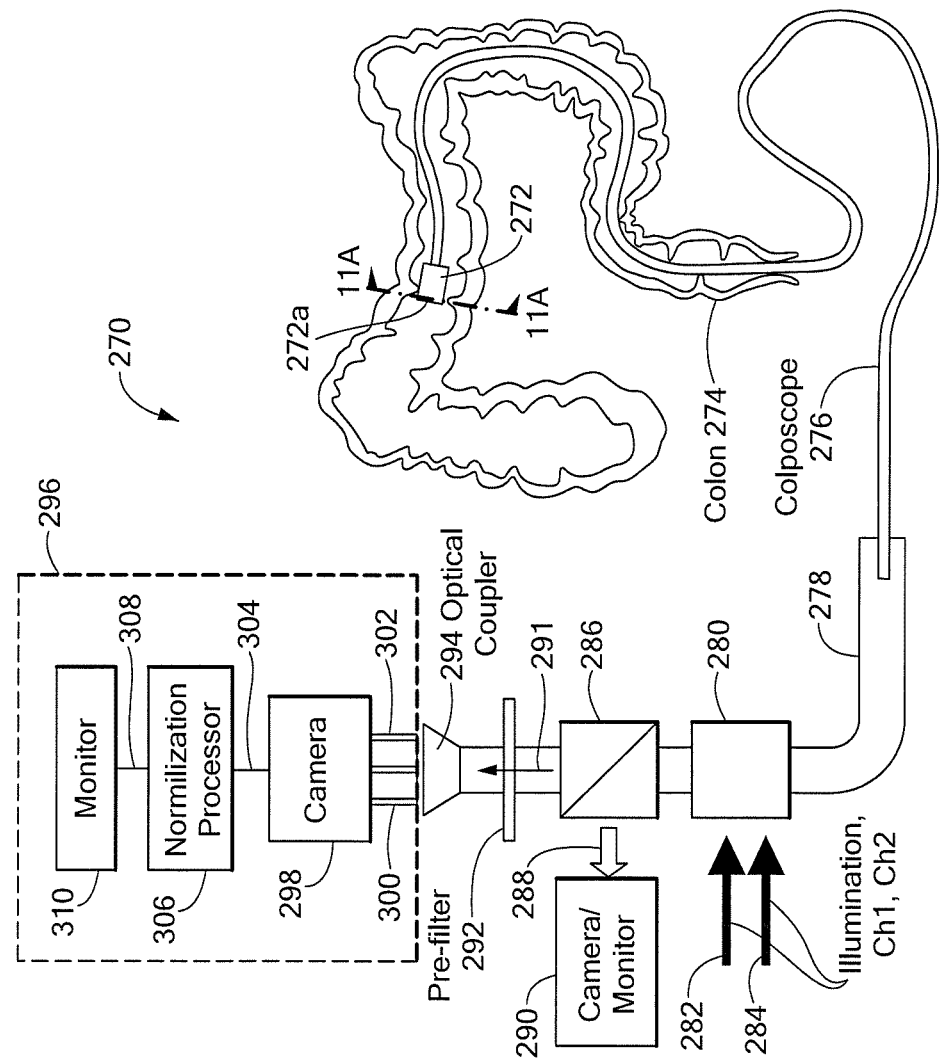
FIG. 11 is a pictorial of a system used for colposcopy having an colposcopic probe.

Referring now to FIG. 11, a system 270, used for colposcopic procedures includes a colposcopic probe 272 (or more simply a probe 272) having a face 272*a*. The face 272*a* of the probe 272 is described in greater detail below in conjunction with FIG. 11A. The probe 272 is inserted into the colon 274 of a patient and is coupled with a colposcope 276 to a colposcope coupler 278. The colposcope 276 includes at least one light fiber (not shown) therewithin.

The colposcope coupler 276 is optically coupled to a light coupler 280, which is adapted to receive light from at least one excitation light source (not shown) and to deliver the light to the colposcope 276. Here, two illumination lights are shown, which are represented by arrows 282, 284. In some embodiments, illumination channel 1 282 provides epi-illumination excitation light at an excitation light wavelength, which is associated with normalization system and method of the present invention. In some embodiments, illumination channel 2 284 also provides epi-illumination excitation light at the same excitation light wavelength. However, in some embodiments, the illumination channel 2 284, can provide light at another wavelength, for example, visible light wavelengths, and is associated with other optical functions, for example, direct colposcopic viewing of visible light as will be apparent from discussion below.

In further embodiments, the epi-illumination channel 2 provides another excitation epi-illumination light at another excitation light wavelength. In these embodiments, the first illumination channel 1 282 is used to excite certain fluorochromes within the colon 274 and the second illumination channel 284 is used to excite other fluorochromes within the colon 274. With this arrangement, two different normalized fluorescence images can be generated.

The colposcope coupler 276 is also optically coupled to a light splitter 288, which is adapted to pass a first portion 288 of received light to a camera/monitor 290. The camera/monitor 280 can be used, for example, for direct colposcopic viewing of visible light during a procedure. A second portion 291 of the received passes through a light filter 292, which is coupled to an optical coupler 294, which directs the second received light 291 to a camera 298. The camera 298 can be the same as or similar to the camera 100 of FIG. 2 or the camera 150 of FIG. 2A. From the above discussion, it should be appreciated that the first and second portions 288, 291, respectively, of the received light can include excitation epi-illumination light at an excitation light wavelength, fluorescence light a fluorescence wavelength, epi-illumination light at another excitation light wavelength, fluorescent light at another fluorescence wavelength, and visible light, in any combination.

The camera 298 is shown to be most similar to the camera 100 of FIG. 1, and has an intrinsic image processor 300 and a fluorescence image processor 302. With this arrangement, the filter 292 can be the same as or similar to the excitation light filter 106 and the fluorescent light filter 108 of FIG. 2.

The camera provides intrinsic excitation epi-illumination images 304 and un-normalized fluorescence epi-illumination images 304 to a normalization processor 306. The normalization processor 306 can be the same as or similar to the normalization processors 30, 70, 80 of FIGS. 1, 1B, and 1C, respectively. The normalization processor 306 is adapted to generate normalized fluorescence epi-illumination images 308 to a monitor 310.

The system 270 is but one example of a system that can be used intra-operatively to provide normalized fluorescence epi-illumination images. Other similar systems can be used to provide normalized fluorescence transillumination images, as described above in conjunction with FIG. 9.

A system similar to the system 270 can be used in a variety of operative procedures, including, but not limited to, a laparoscopic procedure (wherein the probe 272 is a laparoscopic probe), an endoscopic procedure (wherein the probe 272 is an endoscopic probe), a colonoscopic procedure (wherein the probe 272 is a colonoscopic probe), a colposcopic procedure (wherein the probe 272 is a colposcopic probe), an esophageal procedure (wherein the probe 272 is an esophageal probe), a pulmonary procedure (wherein the probe 272 is a pulmonary probe), an oral procedure (wherein the probe 272 is an oral probe), and a dental procedure (wherein the probe 272 is a dental probe). A system similar to the system 270 can be used to image any internal body cavity within a patient.

Referring now to FIG. 11A, the face 272a of the probe 272 (FIG. 11) can include a first illumination port 350 from which the illumination light 282 emanates, and a second illumination port 352 from which the illumination light 282 emanates. The face 272a can also include a port having a camera lens 354, which provides the portions 288, 291 (FIG. 11) of received light to the camera 298 (FIG. 1). The face 272a can also include an irrigation port 356 through which fluid can be pumped into the colon 274 (FIG. 1) or retrieved from the colon 274. The face3 272a can also include a channel 358 through which instruments can be inserted into the colon 274.

The term "optical biopsy" used in conjunction with reference designator 358 is used to indicate an optical method, which is used to non-invasively acquire tissue information similar to the way in which information is obtained by a traditional invasive biopsy (i.e. tissue excision and histological examination). For example, an optical biopsy can be a spectroscopic technique that locally assesses cell nuclear size and density, an in-vivo confocal microscopy technique, or a normalized fluorescence method such as the one described herein. Similar to an invasive biopsy, an optical biopsy is used to characterize a relatively small lesion. A biopsy is used to characterize a relatively small area with high specificity in contrast to so-called "screening" that is associated with large fields of view.

It should be appreciated that all of the ports, and channels of the face 272a are associated with light fibers or channels through the colposcope 276 of FIG. 1.

It will be appreciated from the image examples provided in FIG. 5-8A, that normalized epi-illumination and normalized fluorescence transillumination imagining provide improved images in a variety of applications. Normalized epi-illumination imaging tends to be surface weighted. In other words, surface features can be seen well and with epi-illumination imaging the technique is appropriate for surgical and endoscopic applications. However the sensitivity and imaging resolution of epi-illumination imaging can be reduced for objects that are under the surface, in which case, normalized fluorescence transillumination imaging may be preferred. Normalized fluorescence transillumination imagining can often provide useful images in diffusive volumes to greater depths than normalized fluorescence epi-illumination imaging. This is because normalized fluorescence transillumination imagining has different characteristics than normalized fluorescence epi-illumination imaging. In particular, only a relatively small amount of excitation light is collected in normalized fluorescence transillumination imagining due to attenuation of the excitation light as it passes through the diffusive volume, therefore, any bleed through signal is reduced. Similarly, in normalized fluorescence transillumination imagining, any surface auto-fluorescence is excited by significantly attenuated light compared to normalized fluorescence epi-illumination imaging. These differences yield more uniform volume sampling in transillumination and significantly reduced background signals.

The above-described normalization can improve imaging performance by correcting for the effects of optical property variation in tissues and for variations in the strength of the excitation illumination field. Normalization is well suited for in-vivo investigations and can be implemented as a real time correction so that the user can observe corrected images in real time.

In general, it will be appreciated that un-normalized transillumination images can serve as raw data for conventional tomographic images. When used for improved tomographic imaging, normalized fluorescence transillumination images can provide improved image volume (i.e. increased depth), minimization of surface fluorescence, and reduced sensitivity to variations of transillumination light source optical properties. Due to the use of accurate photon propagation models and subsequent inversion, tomography using normalized images in place of un-normalized images can yield improved three-dimensional quantified maps of fluorescence activity and can correct for depth dependent sensitivities of collected photons. Therefore, tomography is a more integrated approach than either epi-illumination or transillumination planar imaging. Tomography is, however, more complex to implement and uses relatively complex tomographic processing. Tomography also suffers from longer computation times, which tend to make tomography less favored when compared to epi-illumination and transillumination planar approaches, especially when used for real time imaging.

It should be also appreciated that imaging performance can be significantly improved if normalized fluorescence epi-illumination and normalized fluorescence transillumination images and methods are used in combination. Using a combined normalized epi-illumination/normalized transillumination system as shown, for example, in FIGS. 1 and 1B, the sensitivity of epi-illumination imaging to surface activity is retained, but volume sampling (i.e., resolution with depth) capability of transillumination imaging is added.

In both epi-illumination and transillumination systems and methods, normalization can offer certain advantages, including, but not limited to, reduced sensitivity to inhomogeneous illumination field variations and variations in background optical properties. Hardware requirements are only moderately increased for a combined epi-illumination and transillumination system.

All references cited herein are hereby incorporated herein by reference in their entirety.

Having described preferred embodiments of the invention, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:

1. A method of imaging, comprising:
generating incident light including excitation light with an excitation light source, wherein the excitation light source comprises an epi-illumination light source;
directing the incident light toward a tissue;
receiving the incident light with a light detector after the incident light has interacted with a tissue;
receiving emitted light with the light detector, wherein the emitted light is emitted from the tissue;
generating an excitation image of the tissue in response to received incident light, wherein the excitation image is obtained at a wavelength of the excitation light, wherein the excitation light is near-infrared light;
generating an un-normalized emitted light image of the tissue in response to the received emitted light, wherein the un-normalized emitted light image comprises an un-normalized fluorescence epi-illumination image generated at a selected wavelength different than the wavelength of the excitation light; and
dividing the un-normalized emitted light image by the excitation image to generate a normalized emitted light image of the tissue.

2. The method of claim 1, further comprising: inserting a probe into a patient during an operative procedure, wherein the generating the incident light includes transmitting the incident light from the probe, wherein the receiving the incident light includes receiving the incident light with the probe, and wherein the receiving the emitted light includes receiving the emitted light with the probe.

3. The method of claim 2, wherein the operative procedure comprises imaging an internal body cavity of a patient.

4. The method of claim 1, wherein the method comprises a selected one of a laparoscopic imaging method, an endoscopic imaging method, a colonoscopic imaging method, a colposcopic imaging method, an esophageal imaging, method, a pulmonary imaging method, an oral imaging method, and a dental imaging method.

5. The method of claim 1, wherein:
the emitted light comprises fluorescent light associated with the tissue;
the excitation image comprises an excitation epi-illumination image; and
the normalized emitted light image comprises a normalized fluorescence epi-illumination image.

6. The method of claim 5, wherein fluorescent light is generated by at least one of a fluorescent marker which is administered to the tissue and an endogenous tissue fluorescent molecule in response to the excitation light.

7. The method of claim 6, wherein the incident light is substantially at one wavelength.

8. The method of claim 1, wherein the dividing comprises dividing pixel magnitudes of pixels of the un-normalized emitted light image by pixel magnitudes of co-registered pixels of the excitation image.

9. The method of claim 1, wherein the incident light has a wavelength in the range of four hundred to one thousand nanometers and the emitted light also has a wavelength in the range of four hundred to one thousand nanometers, wherein the wavelength of the excitation light is shorter than the wavelength of the emitted light.

10. The method of claim 1, wherein the light detector comprises a charge coupled device camera.

11. The method of claim 1, further including:
generating a first background image of the tissue at generally a same wavelength as the excitation image;
generating a second background image of the tissue at generally a same wavelength as the un-normalized emitted light image;
combining the excitation image and the first background image to provide a noise-reduced excitation image;
combining the un-normalized emitted light image and the second background image to provide a noise-reduced un-normalized emitted light image; and
combining the noise-reduced un-normalized emitted light image and the noise-reduced excitation image to provide a noise-reduced normalized emitted light image.

12. The method of claim 1, wherein the incident light includes one or more wavelengths, and wherein the excitation image is generated by combining excitation images associated with the one or more wavelengths.

13. The method of claim 1, wherein the light detector is disposed on generally a same side of the tissue as the epi-illumination light source.

14. A system for imaging a tissue, the system comprising:
an excitation light source adapted to generate incident light including excitation light, wherein the excitation light source comprises an epi-illumination light source;
a light detector adapted to receive the incident light after the incident light has interacted with the tissue, the light detector further adapted to receive emitted light, wherein the emitted light is emitted from the tissue; and
one or more processors adapted to:
(i) generate an excitation image of the tissue in response to received incident light, wherein the excitation image is obtained at a wavelength of the excitation light, wherein the excitation light is near-infrared light;
(ii) generate an un-normalized emitted light image of the tissue in response to the received emitted light, wherein the un-normalized emitted light image comprises an un-normalized fluorescence epi-illumination image generated at a selected wavelength different than the wavelength of the excitation light; and
divide the un-normalized emitted light image by the excitation image to generate a normalized emitted light image associated with the tissue.

15. The system of claim 14, further comprising:
a probe; and
at least one optical fiber coupled between the probe and the excitation light source and between the probe and the light detector, wherein the at least one optical fiber is adapted to carry the incident light to the probe, to receive the incident light with the probe after the incident light has interacted with the tissue, and to receive the emitted light with the probe.

16. The system of claim 14, further comprising:
a probe configured to image an internal body cavity of a patient.

17. The system of claim 16, wherein the probe comprises a selected one of a laparoscopic probe, an endoscopic probe, a colonoscopic probe, a colposcopic probe, an esophageal probe, a pulmonary probe, an oral probe, and a dental probe.

18. The system of claim 14, wherein:
the emitted light comprises fluorescent light associated with the tissue;
the excitation image comprises an excitation epi-illumination image; and
the one or more processors are adapted to generate the normalized emitted light image as a normalized fluorescence epi-illumination image.

19. The system of claim 18, wherein fluorescent light is generated by at least one of a fluorescent marker which is administered to the tissue and an endogenous tissue fluorescent molecule in response to the excitation light.

20. The system of claim 19, wherein the incident light is substantially at one wavelength.

21. The method of claim 14, wherein the one or more processors are adapted to combine the un-normalized emitted light image and the excitation image by dividing pixel magnitudes of pixels of the un-normalized emitted light image by pixel magnitudes of co-registered pixels of the excitation image.

22. The system of claim 14, wherein the incident light has a wavelength in the range of four hundred to one thousand nanometers and the emitted light also has a wavelength in the range of four hundred to one thousand nanometers, wherein the wavelength of the excitation light is shorter than the wavelength of the emitted light.

23. The system of claim 14, wherein the light detector comprises a charge coupled device camera.

24. The system of claim 14, further including:
a first optical filter coupled to the light detector and adapted to pass the excitation light, wherein the excitation light has a first wavelength; and a second optical filter coupled to the light detector and adapted to pass the emitted light, wherein the emitted light has a second wavelength different from the first wavelength.

25. The system of claim 14, further including an optical filter coupled to the light detector and adapted to pass the excitation light and the emitted light.

26. The system of claim 14, wherein the light detector is further adapted to generate a first background image of the tissue at generally a same wavelength as the excitation image and adapted to generate a second background image of the tissue at generally a same wavelength as the un-normalized emitted light image, and wherein the one or more processors are adapted to:
   (i) combine the excitation image and the first background image to provide a noise-reduced excitation image;
   (ii) combine the un-normalized emitted light image and the second background image to provide a noise-reduced un-normalized emitted light image; and
   (iii) combine the noise-reduced un-normalized emitted light image and the noise-reduced excitation image to provide a noise-reduced normalized emitted light image.

27. The system of claim 14, wherein the incident light includes one or more wavelengths, and wherein the excitation image is generated by combining excitation images associated with the one or more wavelengths.

28. The system of claim 14, wherein the light detector is disposed on generally a same side of the tissue as the epi-illumination light source.

* * * * *